United States Patent [19]
Nadler et al.
[11] Patent Number: 4,853,391
[45] Date of Patent: Aug. 1, 1989

[54] PYRIDO[1,2-A]INDOLES AND THEIR USE AS CARDIOVASCULAR

[76] Inventors: Guy Nadler, 16 Rue de la Fonderie, (35100) Rennes; Jean-Bernard Le Polles, 16 Rue de Primauguet, (35000) Rennes; Marie-Noelle Legave, 8 Rue de Robien, (35850) Geveze, all of France

[21] Appl. No.: 750,038

[22] Filed: Jun. 28, 1985

[30] Foreign Application Priority Data

Jun. 30, 1984 [GB] United Kingdom ................. 8416724

[51] Int. Cl.[4] .................. A61K 31/395; C07D 471/02

[52] U.S. Cl. .................................. 514/294; 514/212; 546/94; 540/597

[58] Field of Search .......................... 546/94; 540/597; 514/294, 212

[56] References Cited

U.S. PATENT DOCUMENTS

| | | | |
|---|---|---|---|
| 4,328,343 | 5/1982 | Vollhardt et al. | 546/94 |
| 4,595,688 | 6/1986 | Maryanoff | 546/94 |
| 4,624,954 | 11/1986 | Jirkovsky et al. | 546/94 |

OTHER PUBLICATIONS

Yoshio et al. J. Am. Chem. Soc. 1981, 103, 6990-2.
Yoshio et al. Chem. Abstracts, vol. 100, p. 175109c, void, vol. 96, 20336z, void, vol. 93, 168461v.
Cole, Susan, Chem. Abstracts, vol. 92, 198605s.
Verpoorte et al., vol. 100 64933x.
Kappe, Chem. Abstracts, vol. 67, 1967; 82039q, Acheson et al. Chem. Abstr. vol. 62, 1965; 16188h-16189a.
Kappe et al., Chem. Abstracts, vol. 99, 1983; 88023n, void, vol. 78, 1973; 111166p.
Thyagarajan et al., Chem. Abstracts, vol. 63, 1965; 4255e.
Allen et al., Chem. Abstracts, 1960; 1534b.
Leaver et al., Chem. Abstracts, 1964; 5454a.
Kobayashi et al., Chem. Abstracts, vol. 88, 1978; 44882k.
Yoshio et al., Chem. Abstracts, vol. 92; 198606t, (1980).
Verpoorte et al., J. Med. Plant Res., 48, (1983), 283-289.

*Primary Examiner*—John M. Ford
*Assistant Examiner*—J. Richter
*Attorney, Agent, or Firm*—Jacobs & Jacobs

[57] ABSTRACT

A pharmaceutical composition comprising a compound of formula (I) or a pharmaceutically acceptable salt thereof:

(I)

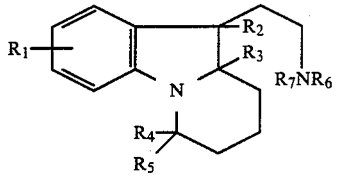

wherein:

$R_1$ is hydrogen, $C_{1-6}$ alkyl, $C_{1-6}$ alkoxy or halogen;

$R_2$ and $R_3$ are both hydrogen or together represent a bond;

$R_4$ is hydrogen and $R_5$ is hydrogen or $R_4$ and $R_5$ together represent an oxo group;

$R_6$ is hydrogen; $C_{1-6}$ alkyl; $C_{3-7}$ cycloalkyl; $C_{3-7}$ cycloalkyl-$C_{1-4}$ alkyl; phenyl or phenyl $C_{1-7}$ alkyl in which the phenyl moiety is optionally substituted by one or two of halogen, ortho-nitro, meta-or para-methoxy, methyl or $NR_8R_9$ wherein $R_8$ and $R_9$ are independently hydrogen or $C_{1-6}$ alkyl or $R_8$ and $R_9$ together are $C_{2-6}$ polymethylen, or 3,4-disubstituted by methylenedioxy or ethylenedioxy; or monocyclic heteroaryl-$C_{1-4}$ alkyl or aliphatic heterocyclyl-$C_{1-4}$ alkyl of up to six ring atoms, the heteroatom(s) being selected from oxygen, sulphur or nitrogen, any amino nitrogen heteroatom optionally $C_{1-4}$ alkyl substituted; and $R_7$ is hydrogen or $C_{1-4}$ alkyl;

and a pharmaceutically acceptable carrier.

22 Claims, No Drawings

PYRIDO[1,2-A]INDOLES AND THEIR USE AS CARDIOVASCULAR

This invention relates to compounds having pharmacological activity, to a process for their preparation and their use as pharmaceuticals.

J. Am. Chem. Soc. 1981, 103, 6990–6992 discloses secocanthine derivatives of formula (A):

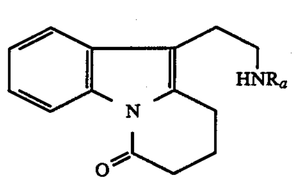

(A)

wherein Ra is hydrogen or benzyl. No pharmacological activity is disclosed for these compounds.

A group of secocanthine derivatives including those of formula (A) have now been discovered to have anti-hypoxic activity and/or activity against cerebral oxygen deficiency.

Accordingly, the present invention provides a pharmaceutical composition comprising a compound of formula (I) or a pharmaceutically acceptable salt thereof:

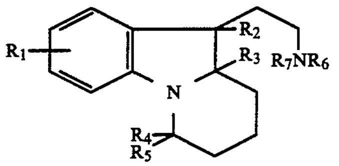

(I)

wherein:

$R_1$ is hydrogen, $C_{1-6}$ alkyl, $C_{1-6}$ alkoxy or halogen;

$R_2$ and $R_3$ are both hydrogen or together represent a bond;

$R_4$ is hydrogen and $R_5$ is hydrogen or $R_4$ and $R_5$ together represent an oxo group;

$R_6$ is hydrogen; $C_{1-6}$ alkyl; $C_{3-7}$ cycloalkyl; $C_{3-7}$ cycloalkyl-$C_{1-4}$ alkyl; phenyl or phenyl $C_{1-7}$ alkyl in which the phenyl moiety is optionally substituted by one or two of halogen, ortho-nitro, meta-or para-methoxy, methyl or $NR_8R_9$ wherein $R_8$ and $R_9$ are independently hydrogen or $C_{1-6}$ alkyl or $R_8$ and $R_9$ together are $C_{2-6}$ polymethylene, or 3,4-disubstituted by methylenedioxy or ethylenedioxy; or monocyclic heteroaryl-$C_{1-4}$ alkyl, aliphatic heterocyclyl or aliphatic heterocyclyl-$C_{1-4}$ alkyl of up to six ring atoms, the heteroatom(s) being selected from oxygen, sulphur or nitrogen, any amino nitrogen heteroatom optionally $C_{1-4}$ alkyl substituted; and $R_7$ is hydrogen or $C_{1-4}$ alkyl;

and a pharmaceutically acceptable carrier.

The compounds of the present invention have anti-hypoxic activity and/or activity against cerebral oxygen deficiency and are therefore useful in treating cerebrovascular disorders and disorders associated with cerebral senility.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment of cerebrovascular disorders and/or disorders associated with cerebral senility in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.1 to 100 mg/kg; and such therapy may extend for a number of weeks or months.

The invention further provides a compound of formula (I) or a pharmaceutically acceptable salt thereof, for use in the treatment of cerebrovascular disorders and/or disorders associated with cerebral senility.

Suitable examples of $R_1$ include hydrogen, methyl, ethyl, n- and iso-propyl, n-, sec-, iso- and tert-butyl, methoxy, ethoxy, fluoro and chloro. $R_1$ is preferably hydrogen or methyl, most preferably hydrogen.

$R_2$ and $_3$ preferably together represent a bond.

$R_4$ and $R_5$ are preferably both hydrogen.

Suitable examples of $R_6$ include hydrogen, methyl, ethyl, n-and iso-propyl, n-, sec-, iso- and tert-butyl, $C_{5-7}$ cycloalkyl, $C_{5-7}$ cycloalkylmethyl, phenyl, benzyl, phenethyl or 1-methyl-2-phenylethyl in which the phenyl moiety is optionally substituted by one or two of fluoro, chloro, bromo, amino, methylamino, ethylamino, neo-pentylamino, dimethylamino, diethylamino, di-isopropylamino, 1-piperidyl, 1-pyrrolidyl, ortho-nitro, meta or para-methoxy, or methyl, or 3,4-disubstituted by methylenedioxy; or pyridyl, thienyl, furyl, or optionally N-methyl substituted piperidyl, pyrryl or pyrrolidinyl. Preferably $R_6$ is benzyl or 1-methyl-2-phenylethyl, optionally monosubstituted in the phenyl moiety by $NR_8R_9$.

Suitable examples of $R_7$ include hydrogen, methyl, ethyl, n- and iso-propyl, n-, sec-, iso- and tert-butyl.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

There is a favourable group of compounds within formula (I) of formula (II) :

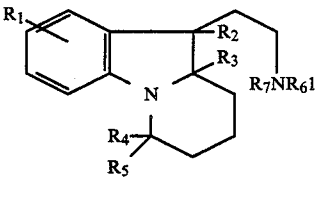

(II)

wherein $R_1$, $R_2$, $R_3$, $R_4$, $R_5$ and $R_7$ are as defined in formula (I) and $R_6{}^1$ is hydrogen, $C_{1-4}$ alkyl, $C_{5-7}$ cycloalkyl, or phenyl $C_{1-7}$ alkyl optionally monosubstituted by fluoro, chloro, bromo, $NR_8R_9$ where $R_8$ and $R_9$ are as defined in formula (I), methoxy or nitro.

Suitable and preferred values for $R_1$, $R_2$, $R_3$, $R_6{}^1$, $R_7$, $R_8$ and $R_9$ are as described under formula (I) for $R_1$, $R_2$, $R_3$, $R_6$, $R_7$, $R_8$ and $R_9$.

There is a sub-group of compounds within formula (II) of formula (IIa):

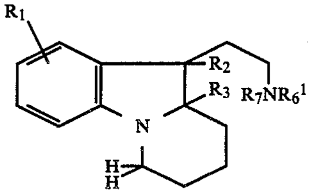

(IIa)

wherein $R_1$, $R_2$, $R_3$, $R_6{}^1$ and $R_7$ are as defined in formula (II).

Suitable and preferred values for the variables are as described for the corresponding variables under formula (I).

There is a sub-group of compounds within formula (IIa) of formula (IIb):

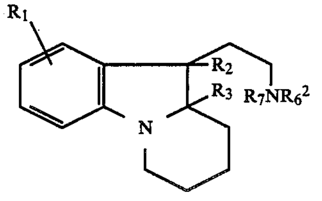

(IIb)

wherein $R_1$, $R_2$, $R_3$ and $R_7$ are as defined in formula (I) and $R_6{}^2$ is phenyl $C_{1-4}$ alkyl optionally mono-substituted by $NR_8R_9$ where $R_8$ and $R_9$ are as defined in formula (I).

Suitable and preferred values for the variables are as described for the corresponding variables under formula (I).

Preferably $R_1$ is hydrogen.

Preferably $R_2$ and $R_3$ represent a bond.

Preferably $R_6{}^2$ is benzyl or 1-methyl-2-phenylethyl optionally meta-or para-substituted by amino optionally substituted by one or two methyl or ethyl groups.

Preferably $R_7$ is hydrogen.

There is a further group of compounds within formula (II) of formula (III):

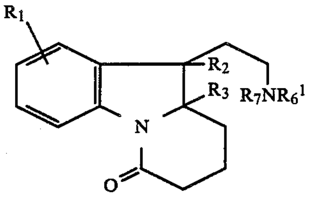

(III)

wherein $R_6{}^1$ is as defined in formula (II) and the remaining variables are as defined in formula (I).

Suitable and preferred values for $R_6{}^1$ and $R_7$ are as described under formulae (II) and IIa).

The invention further provides novel compounds within formula (I), wherein the variable groups are as defined in formula (I) with the proviso that when $R_1$ is hydrogen, $R_2$ and $R_3$ are a bond, $R_4$ and $R_5$ are an oxo group and $R_7$ is hydrogen, $R_6$ is other than hydrogen or benzyl. Such compounds are hereinafter refered to as compounds of formula (IV).

Where compounds of formula (IV) can exist in more than one stereoisomeric form, the invention extends to each of these forms and to mixtures thereof.

The invention further provides a compound of formula (IV) for use as an active therapeutic substance.

A process for the preparation of a compound of formula (I), or a pharmaceutically acceptable salt thereof comprises the conversion of a compound of formula (V):

(V)

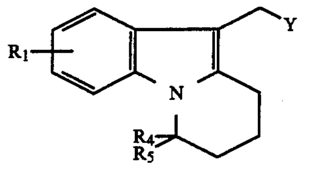

wherein $R_1$, $R_4$ and $R_5$ are as defined in formula (I) and Y is a group convertible to $CH_2NR_6'R_7'$ wherein $R_6'$ is an amino protecting group or $R_6$ as defined in formula (I) with any amino substituent on a phenyl moiety when present in $R_6$ optionally protected, and $R_7'$ is an amino protecting group or $R_7$ as defined in formula (I), into a compound formula (Va):

(Va)

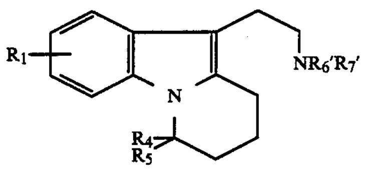

and thereafter, optionally and as necessary, removing any $R_6'$ or $R_7'$ amino protecting group, deprotecting any protected amino substituent in $R_6$, interconverting $R_6$ and/or $R_7$ to other $R_6$ or $R_7$, reducing the $R_2/R_3$ bond and/or, when $R_4/R_5$ is oxo, reducing the oxo group to give a compound wherein $R_4$ and $R_5$ are both hydrogen and/or forming a pharmaceutically acceptable salt.

Y may be conventional amine precursor. Suitable examples include CN, COQ where Q is H or a leaving group such as halo, $C_{1-4}$ alkoxy or carboxylic acyloxy, and $CH_2L$ where L is is $CON_3$, $N_3$, $NO_2$ or X where X is a leaving group such as hydroxy, halo, $C_{1-4}$ alkoxy, $C_{1-4}$ alkanoyloxy, $C_{1-4}$ alkoxycarbonyloxy, tosyloxy or mesyloxy.

The reaction converting the compound of formula (V) into that of formula (Va) may be carried out under the conventional conditions appropriate to the particular group Y in formula (V).

Thus, when Y is $CH_2CON_3$, the conversion is a Curtius degradation carried out conventionally, by heating in dry inert solvent, such as benzene, and then subsequent hydrolysis of the thus formed isocyanate under acid conditions.

When Y is CN, the conversion is a reduction to the primary amine, for example with diborane or with hydrogen over Raney nickel in the presence of ammonia.

When Y is CHO, the conversion is a condensation with hydroxylamine followed by reduction of the thus formed oxime, or is a reductive amination with a primary or secondary amine.

When Y is COQ where Q is a leaving group, the conversion is a nucleophilic substitution by ammonia or a primary or secondary amine under conventional conditions appropriate for leaving group Q, followed by reduction of the resulting amide with e.g. $LiAlH_4$.

When Y is $CH_2N_3$, the conversion is a reduction of the azide to the primary amine with e.g. hydrogen over a metallic catalyst.

When Y is $CH_2NO_2$, the conversion is a reduction of the nitro group to the primary amine with e.g. $LiAlH_4$ or hydrogen over Raney nickel.

When Y is $CH_2X$, the conversion is a nucleophilic substitution by ammonia or a primary or secondary amine under conventional conditions appropriate for the leaving group X. Thus, when X is hydroxy, it is first converted into a good leaving group such as mesylate tosylate or chloride, or it may be substituted by nitrile to yield a compound of formula (V) where $Y{=}CH_2CN$. Hydrolysis and conversion by conventional methods yields a compound where $Y{=}CH_2CON_3$ via the acid as described hereinafter.

In the resulting compound of formula (Va) in the case where $R_6'$ or $R_{7'}$ is an amino protecting group such as $C_{1-6}$ alkoxy carbonyl, aryloxycarbonyl, $C_{1-6}$ alkanoyl or phenyl $C_{1-7}$ alkanoyl, the protecting group may be removed by conventional procedures. Alternatively, alkanoyl or phenylalkanoyl may be converted directly to alkyl or phenyl alkyl $R_6/R_7$ (as appropriate) by reduction, e.g. with $LiAlH_4$ and $AlCl_3$.

When $R_6'$ is an $R_6$ group with a protected amino moiety, again the protecting group may be removed conventionally or the protected $R_6$ be converted to the desired $R_6$ group by reduction as in the preceding paragraph.

The interconversion of an $R_6/R_7$ hydrogen atom may be carried out by conventional amine alkylation or, more preferably, by acylation followed by reduction of the amide, or by reductive alkylation.

Acylation may be carried out using the appropriate acyl chloride or anhydride and the subsequent reduction of the resulting amide with $LiAlH_4$ in the presence of $AlCl_3$.

The invention provides a process for the preparation of a compound of the formula (IIa) or a pharmaceutically acceptable salt thereof in which $R_1$ is hydrogen and $R_6^1$ is other than hydrogen which process comprises the alkylation of a compound of the formula (Vb):

(Vb)

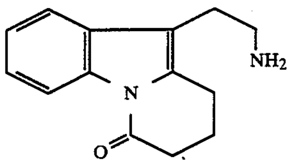

followed by, or simultaneously with, the reduction of the $R_4/R_5$ oxo group and, optionally, the reduction of the $R_2/R_3$ double bond, and/or the formation of a pharmaceutically acceptable salt.

The alkylation may be carried out as described above for the interconversion of an $R_6/R_7$ hydrogen atom.

The invention also provides intermediates of the formula (Vc):

(Vc)

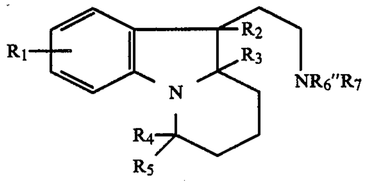

wherein $R_6''$ is phenyl $C_{1-7}$ alkanoyl optionally substituted as defined for the phenyl moiety in $R_6$ of formula (I) and the remaining variables are as defined in formula (I).

Suitable and preferred values for the variables in formula (Vc) are as described for the corresponding variables under formula (I).

The reductive alkylation procedure is preferably carried out by heating with the aldehyde or ketone in an organic acid, such acetic acid, then reducing the product in situ using an alkaline borohydride such as sodium borohydride or cyanoborohydride. The reaction can also be carried out in an alcohol, in which case the reduction can be carried out either chemically, for example with a borane such as trimethylammoniumborane or an alkaline borohydride or with hydrogen in the presence of a catalyst such as Raney nickel. It is also possible to use an aprotic solvent, for example an aromatic solvent such as benzene or toluene, the water-formed being eliminated either at room temperature by means of a drying-agent or under reflux heating of the solvent by means of a Dean-Stark water-separator; the reduction can then be expediently carrried out with hydrogen in the presence of a catalyst such as palladiated carbon or platinum oxide. These methods may be subject to certain limitations, depending on the nature of the aldehyde or ketone used.

It is also possible to use a more universal method. For example, the $R_6/R_7$ hydrogen compound and the aldehyde or ketone to be condensed are dissolved in a mixture of solvents which can advantageously be a methanol-dichloromethane mixture in the presence of a complex reducing agent such as quaternary ammonium cyanoborohydride or, more simply, an alkaline cyanoborohydride solubilised by a phase-transfer agent, for example sodium cyanoborohydride and aliquat 336(Cf. Hutchins, R. O. and Markowitz, M., Journal of Organic Chemistry 1981, 46, pp. 3571–3574).

It will be appreciated that compounds of formula (I) wherein $R_6$ is substituted phenyl or phenyl $C_{1-7}$ alkyl may be interconverted by conventional procedures including aromatic substituents. For example a compound of formula (I) wherein $R_6$ is benzyl substituted by amino may be prepared from a compound wherein $R_6$ is benzyl substituted by nitro, by catalytic reduction, for example in the presence of Raney nickel.

A compound of formula (I) wherein $R_6$ is benzyl substituted by substituted amino may be prepared from the corresponding amine by conventional procedures. Thus when $R_8$ or $R_9$ is an alkyl group, conventional amine alkylation, acylation followed by reduction, or reductive alkylation may be employed.

The invention further provides compounds of the formula (Vd):

(Vd)

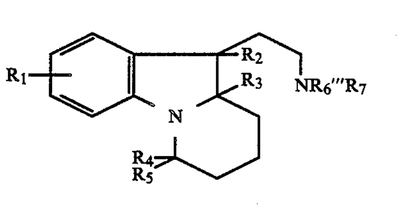

wherein $R_6'''$ is phenyl $C_{1-4}$ alkyl or phenyl $C_{1-4}$ alkanoyl mono-substituted by a protected amino group or mono-substituted in the meta or para position by a nitro group, and the remaining variables are as defined in formula (I). Suitable and preferred values for the variables in formula (Vd) are as described for the corresponding variables under formula (I).

Compounds of formula (Vd) are intermediates in the preparation of those compounds of formula (IIb) where $R_6^2$ is phenyl $C_{1-4}$ alkyl substituted by $NR_8R_9$ where $R_8$ and $R_9$ are as defined in formula (I).

When $R_6$ in formula (I) is optionally substituted phenyl, introduction of the phenyl moiety cannot in general be achieved by conversion from $R_6$ hydrogen as discussed above. Instead, the conversion of Y to $C_2NR_6'R_7'$ will be carried out using aniline as the primary amine, preferably by reductive amination of a Y aldehyde group. However, the presence of an electon withdrawing substituent such as $NO_2$ on the phenyl ring will permit nucleophilic aromatic substitution of the ring by a compound of formula (I) where $R_6$ is hydrogen with a halogen atom, preferably fluoro, as the leaving group in strong base such as pyridine.

The reduction of the $R_2/R_3$ bond may be carried out conventionally by the use of an alkaline borohydride in a polar aprotic solvent such as dimethylsulphoxide or by nitromethane in the presence of a strong organic acid such as methanesulphonic acid or in pure trifluoroacetic acid. Alternatively the bond may be reduced catalytically with hydrogen over platinum oxide catalyst in a solvent permitting protonation of the indolic nitrogen, such as ethanol containing fluoroboric acid or acetic acid containing trifluoroacetic acid.

When $R_4$ and $R_5$ together form an oxo group, compounds wherein $R_4$ and $R_5$ are both hydrogen may be prepared by reduction of the $R_4/R_5$ oxo group in formula (I) using a mixed hydride complexed with a Lewis acid, for example, the complex aluminium lithium aluminium chloride hydride in an inert solvent such as diethyl ether. When an $R_6$ or $R_7$ group other than hydrogen is introduced initially by acylation to give the amide, simultaneous reduction of the $R_4/R_5$ oxo group and the amide moiety may be effected by appropriate choice of reducing agent, for example the mixed hydride complexed with a Lewis acid just described.

When $R_2$ and $R_3$ together form a bond and $R_4$ and $R_5$ together form an oxo group, simultaneous reduction of the double bond and the oxo group may be effectec by the use of an alkaline borohydride as described above for the reduction of an $R_2/R_3$ bond.

It will be appreciated that these conversions may take place in any desired or necessary order.

Pharmaceutically acceptable salts of the compounds of formula (I) may be formed conventionally by reaction with the appropriate acid such as described above under formula (I).

The invention therefore provides a process for the preparation of a compound of formula (IV), or a pharmaceutically acceptable salt thereof which process comprises the conversion of the compound of formula (V) as hereinbefore defined to the compound of formula (Va) as hereinbefore defined and thereafter, optionally and as necessary, removing any $R_6'$ or $R_7'$ amino protecting group, interconverting $R_6$ and/or $R_7$ hydrogen to other $R_6$ or $R_7$, reducing the $R_2/R_3$ bond and/or, when $R_4/R_5$ is oxo, reducing the oxo group to give a compound wherein $R_4$ and $R_5$ are both hydrogen and/or forming a pharmaceutically acceptable salt.

Compounds of formula (V) in which Y is $CH_2CON_3$ may be prepared by the formation of the acid chloride followed by reaction of azide ion on an acid of formula (VI):

(VI)

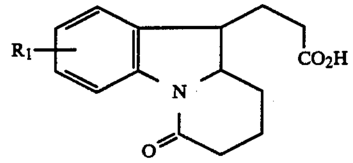

This method is described in J. Am. Chem. Soc. 1981, 103, 6990–6992.

Acids of formula (VI) are known or may be prepared by conventional methods. For example, a phenylhydrazine is condensed with 4-oxoazelaic acid (ref. Von Pechmann et. al. Berichte 1904, 37, p 3816). The hydrazone thus obtained is subjected to a Fischer cyclisation to give the acid of formula (VI).

Compounds of formula (V) in which $R_4$ and $R_5$ are both hydrogen may be prepared by the reaction of a compound of formula (VII):

(VII)

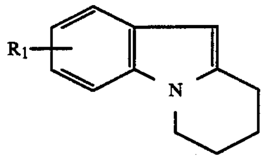

with (i) $ClCOCOR_{10}$, where $R_{10}$ is alkoxy such as ethoxy or halo such as chloro, followed by reduction with $LiAlH_4$ to give a compound of formula (V) where Y is $-CH_2OH$;

(ii) $CH_2{=}CH{-}R_{11}$, where $R_{11}$ is a 1-carbonyl containing group or cyano, under basic conditions, followed by reaction on the resulting acid group by azide ion as described above, to give a compound of formula (V) where Y is $-CH_2CON_3$;

(iii) formaldehyde in the presence of dimethylamine followed by reaction of cyanide ion on the resulting tertiary amine, if necessary after quaternization, to give a compound of formula (V) where Y is —CN;

(iv) $CH_2{=}CHNO_2$ under basic conditions to give a compound of formula (V) where Y is $CH_2NO_2$.

Compounds of formula (VII) can be prepared according to Hans Zimmer, J. Heterocyclic Chemistry 21, 623(1984).

Alternatively, compounds of formula (V) in which $R_4$ and $R_5$ are both hydrogen and Y is $-CH_2CN$, may be prepared by homologation and reduction of a compound of formula (VIII):

(VIII)

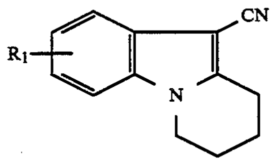

prepared according to D. N. Reinhoudt et al., Tetrahedron Letters 26 (5) 1985, 685–8. The nitrile is first reduced to the amine which is quaternised and reacted with cyanide ion to give the relevant compound of formula (V).

In the formulae (VI), (VII) and (VIII) above, $R_1$ is as defined in formula (I).

The following examples and pharmacological data illustrate the invention and the following descriptions illustrate the preparation of intermediates thereto.

DESCRIPTION 1

2-Methyl-6-oxo-6,7,8,9-tetrahydropyrido[1,2-a]-indole-10-propionic acid (D1)

D1

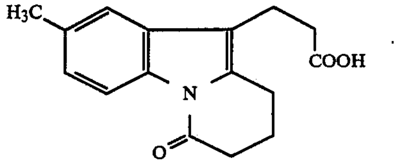

50 g (0.31 mole) paratolylhydrazine hydrochloride and 80 g (0.39 mole) 4-oxoazelaic acid were stirred for 1 hour at room temperature in 900 ml 10% sulphuric acid and then the mixture was heated under reflux for 3 hours. After cooling to room temperature the mixture was extracted with methylene chloride and the organic phase was washed with water, treated with activated charcoal and then dried over magnesium sulphate. It was then concentrated to dryness and crystallised in isopropylether, giving 46 g of a beige crystalline solid D1 of m. pt. 152°–153° C.

IR (KBr)$\nu$=3200–2500; 1725; 810 $cm^{-1}$.

UV ($C_2H_5OH$)$\lambda$ max=248; 275 (sh); 297; 306 nm.

Mass spectroscopy empirical formula: $C_{16}H_{17}NO_3$.

Molecular weight found: 271.1142, theoretical: 271.1157.

m/e (% relative intensity) 271 ($M^+$, 100); 212(82); 184(84).

DESCRIPTION 2

6-Oxo-6,7,8,9-tetrahydropyrido[1,2-a]indole-10-propionic acid (D2)

D2

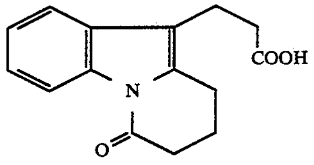

This compound has been described by Y. Ban in J. Amer. Chem. Soc. 1981, 103 (23), pp. 6690–6992. Melting-point 163°–165° C.

IR (KBr)$\nu$=3200–2500; 1700; 755 $cm^{-1}$.

DESCRIPTION 3

2-Methyl-6-oxo-6,7,8,9-tetrahydropyrido[1,2-a]indole-10-propionic acyl azide (D3)

D3

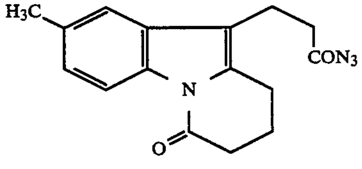

(a) Acid chloride: 1.5 g oxalyl chloride (11.5 mmoles) and 1 drop of DMF were added dropwise to a suspension of 1.5 g (5 mmoles) of the acid Description 1 in 4 ml benzene. When the liberation of vapours slowed down the mixture was heated for 30 minutes at 60°-70° C. The brown solution thus obtained was concentrated to dryness in vacuo, leaving a residue of maroon-coloured crystals, which were used as they were for stage (b).

(b) Acyl azide: The crude acid chloride from stage (a) was dissolved in 12 ml dry acetone and added dropwise to an ice-cooled solution of 0.4 g sodium azide in 1 ml water and stirred for a further 30 minutes at 0° C., then for 30 minutes at room temperature. The mixture was then diluted with 25 ml water, the precipitate formed was filtered off, washed with water and then dried in vacuo at room temperature, giving a white crystalline solid D3.

DESCRIPTION 4

6-Oxo-10-(2-aminoethyl)-6,7,8,9-tetrahydropyrido[1,2-a]indole hydrochloride (D4)

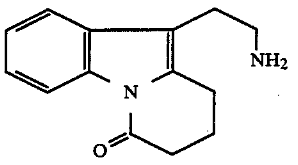

D4

The acid Description 2 was converted to the corresponding azide by the process of Description 3. 56.3 mmoles crude azide was dissolved in 70 ml dry benzene and heated under reflux for 40 minutes. There was a substantial liberation of nitrogen and the solution turned black. 100 ml benzene and 24 ml concentrated HCl were then added and heated under reflux for 1 hour. There was a substantial liberation of gas/vapours, and then a precipitate was formed. The solution was then concentrated to dryness, giving the crude amine hydrochloride. Recrystallisation in a 4/1 mixture of ethanol/water produced a white crystalline solid D4 described by Y. Ban(ref.cited) of m.pt. 330°-335° C. (decomposition).

IR (KBr)ν=3200-2400; 1700; 745 $cm^{-1}$.

UV (ethanol)λmax=243; 267; 292; 302 nm.

DESCRIPTION 5

6-Oxo-10-[2-(3-nitrobenzoyl)aminoethyl]-6,7,8,9-tetrahydropyrido[1,2-a]indole (D5)

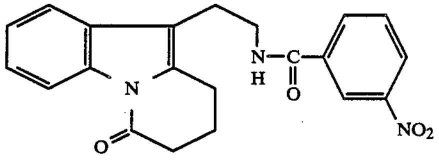

D5

A solution of 19 g m-nitrobenzoyl chloride in 50 ml $CHCl_3$ (chloroform) was added dropwise to an ice-cooled suspension of 24 g compound D4 and 25 g triethlamine in 300 ml $CHCl_3$. After total solubilisation a precipitate was formed. The mixture was left to stand for 4 hours at room temperature, then filtered. The cyrstals were washed with $CH_2Cl_2$, water and ether. 25.2 g of D5 was obtained.

m.pt 215° C.

IR(KBr)ν=3260; 3100-2800; 1690; 750; 720; 680; 650 $cm^{-1}$.

DESCRIPTION 6

6-Oxo-10-[2-(3-aminobenzoyl)aminoethyl]-6,7,8,9-tetrahydropyrido[1,2-a]indole hydrochloride (D6)

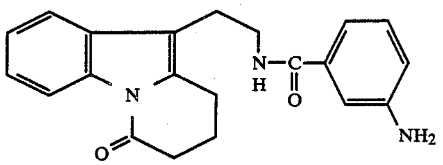

D6

Compound D5 (29 g) was hydrogenated at room temperature at a pressure of 10 bar for 12 hours in 500 ml DMF in the presence of 5 g of Raney nickel. The catalyst was filtered off, the DMF concentrated and the amine acidified with ethanol/hydrochloric acid, giving 16 g of D6.

m.pt 240° C.

IR(KBr)ν=3340; 3000-2500; 1660; 760 $cm^{-1}$.

M.S. empirical formula $C_{21}H_{21}N_3O_2$.

M.W. found: 347.1635; theory 347.163366.

m/e (% relative intensity) 347(M+, 20); 211(100); 198(11); 172(27).

DESCRIPTION 7

6-Oxo-10-[2-(4-nitrophenyl)aminoethyl]-6,7,8,9-tetrahydropyrido[1,2-a]indole (D7)

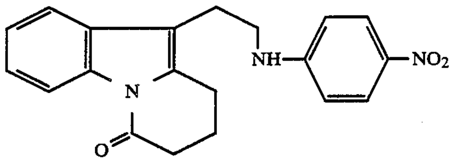

(D7)

13 g Compound D4 and 7 g 1-fluoro-4-nitrobenzene were heated under reflux for 16 hours in 100 ml pyridine. 12 g crystals of D7 were obtained after working up.

DESCRIPTION 8

6-Oxo-10-[2-(3-pivaloylaminobenzoyl)aminoethyl]-6,7,8,9-tetrahydropyrido[1,2-a]indole (D8)

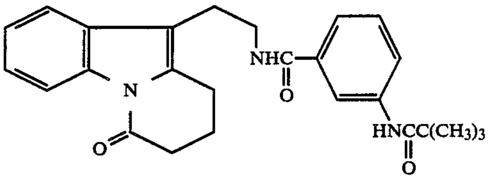

(D8)

8.2 g Compound D6 and 5 g triethylamine in 100 ml $CHCl_3$ were treated cold (ice) with a solution of 2.85 g pivaloyl chloride in 50 ml $CHCl_3$ in the conventional manner but the organic solution was decolourised with activated charcoal before concentrating to dryness. The product crystallised in ethyl acetate, giving 6.6 g of crystals D8.

m.pt.=205° C.

IR(KBr)ν=3350; 3000-2800; 1680; 1650 $cm^{-1}$.

DESCRIPTION 9

6-Oxo-10-[2(3-acetamidobenzoyl)aminoethyl]-6,7,8,9-tetrahydropyrido[1,2-a]indole (D9)

D9

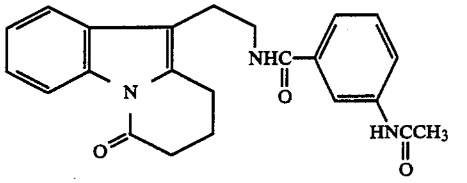

18 g Compound D6 and 16 g triethlamine in 200 ml $CHCl_3$ were treated cold (ice) with a solution of 7 g acetylchloride in 100 ml $CHCl_3$, left to stand overnight at room temperature and then worked up to give 18 g of compound D9.

DESCRIPTION 10

6-Oxo-10-[2-(3-piperidinobenzoyl)aminoethyl]-6,7,8,9-tetrahydropyrido[1,2-a]indole (D10)

D10

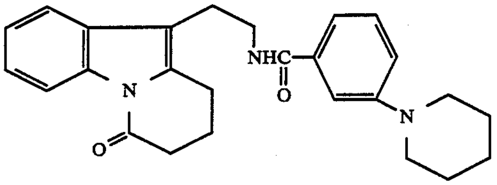

15 g Compound D6, 11 g 1,5-dibromopentane, 20 g powdered potassium carbonate ($K_2CO_3$) and 16 g potassium iodide (KI) were heated for 24 hours at 65° C. in 175 ml DMF, cooled, filtered, concentrated to dryness and the residue taken up in $CH_2Cl_2$, which was then washed with water until neutral, concentrated and made to crystallise in a mixture of acetone and ethyl acetate, giving 8 g of crystals of compound D10.

DESCRIPTION 11

6-Oxo-10-[2-(3-diisopropylaminobenzoyl)aminoethyl]-6,7,8,9-tetrahydropyrido[1,2-a]indole (D11)

(D11)

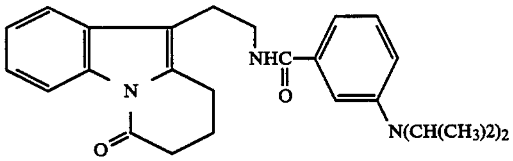

10 g Compound D6, 11 g iodo-2-propane, and 13.5 g powdered $K_2CO_3$ were heated for 24 hours at 90° C. in 150 ml DMF, then cooled, filtered, the filtrate concentrated, taken up in methylene chloride and washed with water until neutral. The concentration left 4.5 g of crude compound D11.

DESCRIPTION 12

6-Oxo-10-[2-(3-formamidobenzoyl)aminoethyl]-6,7,8,9-tetrahydropyrido[1,2-a]indole (D12)

(D12)

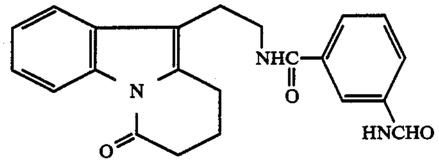

10 g Compound D6 was added at 0° C. to the formic-acetic mixed anhydride prepared from 7.5 g formic acid and 3.5 g acetic anhydride. 5 ml DMF was added to the mixture and after 30 minutes at 0° C. it was left for 3 hours at room temperature. After working-up the oil was ground in acetone, giving 7.9 g crystals of D12.

DESCRIPTION 13

6-Oxo-10-[2-(3-pyrrolidinobenzoyl)aminoethyl]-6,7,8,9-tetrahydropyrido[1,2-a]indole (D13)

(D13)

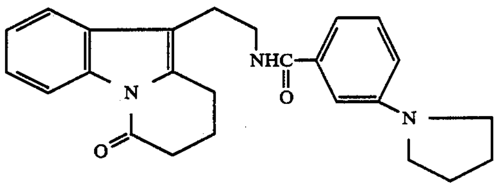

9.3 g Compound D6, 12 g $K_2CO_3$, 14 g KI, 6.2 g 1,4-dibromobutane and 100 ml DMF were heated for 20 hours at 65° C. After working-up the oil obtained was chromatographed on 500 g silica and eluted with a 2:1 mixture of $CH_2Cl_2$:ethyl acetate, giving 8.6 g white crystals of D13.

DESCRIPTION 14

6-Oxo-10-(2-benzylaminoethyl)-6,7,8,9-tetrahydropyrido[1,2-a]indole hydrochloride (D14 )

D14

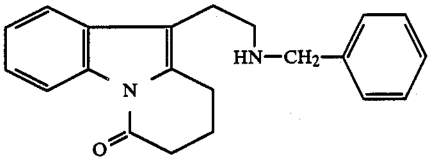

4 g (17 mmoles) Compound D4, 6.2 g benzaldehyde were dissolved in 40 ml glacial acetic acid and stirred for 1 hour at room temperature, then 1 g $NaBH_4$ was added in small fractions, taking care to ensure that the temperature did not exceed 25° C. The reaction was monitored with thin-layer chromatography, and benzaldehyde and/or reducing agent was added if required. When the reaction was completed the mixture was diluted with 20 volumes of water, extracted with methylene chloride, dried, concentrated, the residue was taken up in 400 ml ether and the flakey precipitate formed was removed. The ether solution was acidified with ethanolic hydrochloric acid and the precipitate obtained was filtered off, washed with ether and dried in the oven in vacuo, giving 6 g of white crystals of D14 which were recrystallised in ethanol, after which their m. pt. was 221°-222° C.

IR (KBr)$\nu$=3100-2300; 1710; 760; 750; 700 $cm^{-1}$.

UV ($CH_3OH$)$\lambda$ max=242; 262; 292; 300 nm.

M.S. empirical formula $C_{21}H_{22}N_2O$.

M.W. found: 318.1727; theory: 318.1732.

m/e (% relative intensity) 318 ($M^-$, 4); 199 (50); 170 (11); 144 (7); 143 (7); 120 (85); 91 (100).

DESCRIPTION 15

6-Oxo-10-[2-(4-nitrobenzyl)aminoethyl]-6,7,8,9-tetrahydropyrido[1,2-a]indole hydrochloride (D15)

D15

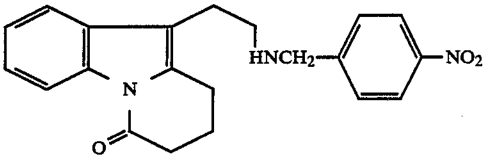

16 g Compound D4 and 10 g 4-nitrobenzaldehyde were stirred at room temperature for 24 hours with 1.15 g $NaBH_3CN$ and 0.6 g aliquat 336 in 400 ml $CH_2Cl_2$:$CH_3OH$(5:2). The mixture was concentrated, the residue taken up in $CH_2Cl_2$ and the solution washed with 100 ml water, dried over $MgSO_4$, concentrated, the residue dissolved in acetone, the solution dried and acidified with ethanol/HCl to produce 10 g green crystals of D15. m.pt=245° C. (decomposition).

IR(KBr) $\nu$=3000-2300; 1690; 760; 750; 695 $cm^{-1}$.

UV($CH_3OH$)$\lambda$max=206; 242; 260; 292; 302 nm.

M.S. empirical formula: $C_{21}H_{21}N_3O_3$.

M.W. found: 363.1588; theory: 363.1582.

m/e(% relative intensity) 363($M^+$, 3); 361(3); 331(3); 207(3); 199(100); 170(22.2); 165(34.9); 144(12.7); 143(15.8); 136(25.4); 106(28.6).

DESCRIPTION 16

6-Oxo-[2-benzoylaminoethyl]-6,7,8,9-tetrahydropyrido[1,2-a]indole (D16)

(D16)

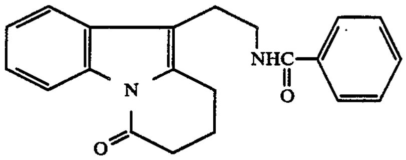

To 2.6 g of the Compound D4 in suspension in 20 ml chloroform and 2.3 g triethylamine was added fraction by fraction, at 0° C., 1.4 g benzoic acid chloride, giving, after treatment 2.7 g white crystals of D16.

m.pt.=164° C.

IR(KBr)$\nu$=3100-2800; 1710; 770; 760; 700 $cm^{-1}$.

UV($CH_3OH$)$\lambda$ max=212; 246; 268(sh); 295; 304 nm.

DESCRIPTION 17

6-Oxo-10-[2-(3-dimethylaminobenzoyl)aminoethyl]-6,7,8,9-tetrahydropyrido[1,2-a]indole (D17)

(D17)

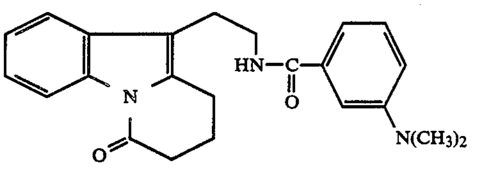

A suspension of 10 g 3-dimethylaminobenzoic acid and 5 g pyridine in 100 ml CS was added to a solution of 12.5 g $PCl_5$ in 125 ml $CS_2$ cooled in an ice-bath. The mixture was left at room temperature for 2 hours then heated under reflux and the pyridine hydrochloride was filtered off from the hot mixture. The $CS_2$ was concentrated and dissolved in 150 ml dry $CHCl_3$. This solution of acid chloride was added dropwise to a suspension of 12 g of the Compound D4 and of 10 g triethylamine in 150 ml $CHCl_3$ cooled in an ice-bath; after treatment and crystallisation in ethylacetate, 8.4 g white crystals of amide D17 was obtained, m. pt. 136° C.

IR(KBr)$\nu$=3260; 3100-2500; 1690; 760; 750; 680 $cm^{-1}$.

DESCRIPTION 18

6-Oxo-10-[2-(4-acetylaminobenzyl)aminoethyl]-6,7,8,9-tetrahydropyrido[1,2-a]indole hydrochloride (D18)

(D18)

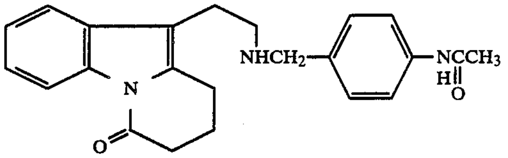

8 g Compound D4 and 5.4 g 4-acetamidobenzaldehyde treated by the proces of Description 15 gave 6 g bright green crystals of D18.

m.pt.>300° C.

IR(KBr)$\nu$=3300-2400; 1710; 800; 770; 750 $cm^{-1}$.

UV($CH_3OH$)$\lambda$max=210; 245; 292; 300 nm

M.S. empirical formula: $C_{23}H_{25}N_3O_2$

M.W. found: 375.1942 theory; 375.1945.

m/e. (% rèlative intensity) 375($M^+$, 2); 373(3, 4); 199(53); 177(20); 170(17); 148(100); 106(49).

DESCRIPTION 19

2-Methyl-6-oxo-10-(2-benzoylaminoethyl)-6,7,8,9-tetrahydropyrido [1,2-a]indole (D19)

(D19)

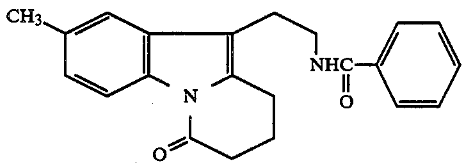

11 g Compound E1 in 100 ml chloroform and 8.9 g triethylamine treated with 5.6 g benzoylchloride produced, after treatment, 11.2 g white crystals of D19, m.pt. 171° C.

EXAMPLE 1

2-Methyl-6-oxo-10-(2-aminoethyl)-6,7,8,9-tetrahydropyrido[1,2-a]indole hydrochloride (E1)

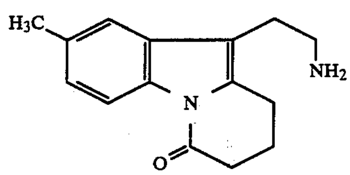

(E1)

56.3 mmoles crude azide from Description 3 was dissolved in 70 ml dry benzene and heated under reflux for 40 minutes. There was a substantial liberation of nitrogen and the solution turned black. 100 ml benzene and 24 ml concentrated HCl were then added and heated under reflux for 1 hour. There was a substantial liberation of gas/vapours, and then a precipitate was formed. The solution was then concentrated to dryness, giving the crude amine hydrochloride. Recrystallisation in a 4/1 mixture of ethanol/water gave a white crystalline solid E1.

m.pt. 305°-310° C. (decomposition).

IR(KBr)ν=3300-2400; 1710; 815 $cm^{-1}$.

UV (ethanol)λmax=245; 270(sh); 295; 304 nm.

Mass spectroscopy empirical formula: $C_{15}H_{18}N_2O$

Molecular weight found: 242.1418; theory: 242.1419. m/e (% relative intensity) 242 (M+, 28); 213 (100); 184 (65).

EXAMPLE 2

6-Oxo-10-(2-isopropylaminoethyl)-6,7,8,9-tetrahydropyrido [1,2-a]indole hydrochloride (E2)

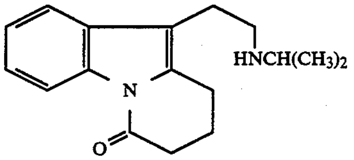

(E2)

4 g Dry acetone was added to 4 g (17 mmoles) of the compond D4 dissolved in 40 ml glacial acetic acid and stirred for 1 hour at room temperature, then 1 g $NaBH_4$ was added in small fractions, taking care to ensure that the temperature did not exceed 25° C. The reaction was monitored with thin-layer chromatography, and acetone and/or reducing agent was added if required. When the reaction was completed the mixture was diluted with 20 volumes of water, extracted with methylene chloride, dried, concentrated, the residue was taken up in 400 ml ether and the flakey precipitate formed was removed. The ether solution was acidified with ethanolic hydrochloric acid and the precipitate obtained was filtered off, washed with ether and dried in the oven in vacuo, giving 4.5 g white crystals of E2 m. pt. 244°-246° C.

IR (KBr)ν=3100-2300; 1700; 745 $cm^{-1}$.

UV($C_2H_5OH$)λmax=242; 267; 292; 302 (sh) nm.

Mass spectroscopy empirical formula $C_{17}H_{22}N_{2}O$.

Molecular weight found 270.1718; theory: 270,1732 m/e (% relative intensity) 270 (M+, 39); 199 (26); 198 (100); 169 (29); 144 (27).

EXAMPLE 3

6-oxo-10-(2-cyclopentylaminoethyl)-6,7,8,9-tetrahydropyrido[1,2-a]indole hydrochloride (E3)

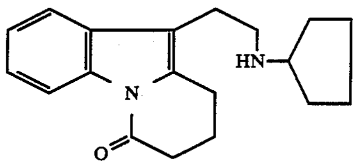

E3

7 g (26 mmoles) Compound D4, 2.7 g (32 mmoles) cyclopentanone, 1 g (6 mmoles) $NaBH_3CN$ and 6.5 g (16 mmoles) aliquat 336 were dissolved in 500 ml of a 5:2 mixture of methylene chloride and methanol and stirred for 48 hours at room temperature. The mixture was filtered, concentrated and then chromatographed on 400 g silica. The principal fraction was concentrated, dissolved in ether and acidified with ethanolic hydrochloric acid. The precipitate obtained was filtered off, washed with ether and dried in vacuo, giving 4.1 g white crystals of E3, m. pt. 152° C.

IR (KBr)ν=3100-2500; 1710; 770; 760; $cm^{-1}$.

UV(Methanol)λmax=242; 265; 293; 302 nm.

M.S. empirical formula $C_{19}H_{24}N_2O$.

Mol. weight found: 296.1888, theory: 296.1888 m/e (% relative intensity) 296 (M+, 5.9); 199 (23); 98 (100).

EXAMPLE 4

6-Oxo-10-[2-(cyclohexylmethyl)aminoethyl]-6,7,8,9-tetrahydropyrido[1,2-a]indole hydrochloride (E4)

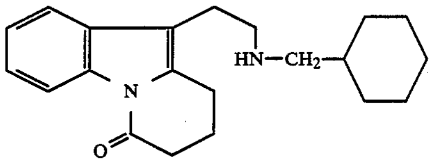

E4

4 g Compound D4 and 1.7 g cyclohexane carboxaldehyde treated by the process of Example 3 produced 3 g white crystals of E4. m. pt. 184°-186° C.

IR (KBr)ν=3100-2300; 1705; 780; cm.

UV ($CH_3OH$)λmax=242; 265; 292; 302 nm.

M.S. empirical formula $C_{21}H_{28}N_2O$.

Molecular weight found: 324.2203; theory: 324.2201. m/e (% relative intensity) 324 (M+5); 199 (30); 170 (7); 126 (100).

EXAMPLE 5

6-Oxo-10-[2-(4-fluorobenzyl)aminoethyl]-6,7,8,9-tetrahydropyrido[1,2-a]indole hydrochloride (E5)

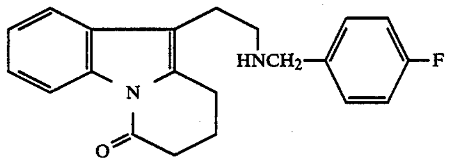

(E5)

7 g (26 mmoles) Compound D4 and 4 g (32 mmoles) 4-fluorobenzaldehyde treated by the process of Example 3 gave 3.1 g beige crystals of E5, m. pt. 184°-185° C.

IR (KBr)ν=3100-2300; 1715; 770; 750 $cm^{-1}$.

UV($CH_3OH$)λ=210; 242; 264; 292; 302 nm

M.S. empirical formula $C_{21}H_{21}N_2OF$.

M.W. found: 336.1636; theory: 336.1637. m/e (% relative intensity) 336 (M+, 5); 199 (66); 170 (14); 144 (9); 138 (58); 109 (100).

EXAMPLE 6

6-Oxo-10-[2-(4-chlorobenzyl)aminoethyl]-6,7,8,9-tetrahydropyrido[1,2-a]indole hydrochloride (E6)

(E6)

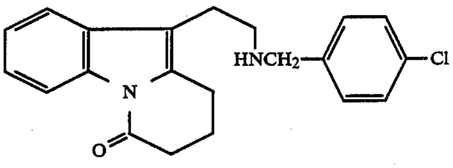

5 g (19 mmoles) Compound D4 and 3 g 4-chlorobenzaldehyde treated by the process of Example 3 gave 4 g white crystals of E6, m. pt. 251°-253° C.

IR(KBr)ν=3100-2300; 1700; 760 $cm^{-1}$.

UV($CH_3OH$)λmax=224; 242; 265; 290; 302 nm

M.S. empirical formula $C_{12}H_{21}N_2OCl$.

M.W. found: 352.1344; theory: 352.1342 m/e (% relative intensity) 352 (M+, 5); 199(100); 170 (34); 154 (100); 143 (26); 125 (76).

EXAMPLE 7

6-Oxo-10-[2-(4-dimethylaminobenzyl)aminoethyl]-6,7,8,9-tetrahydropyrido[1,2-a]indole dihydrochloride (E7)

(E7)

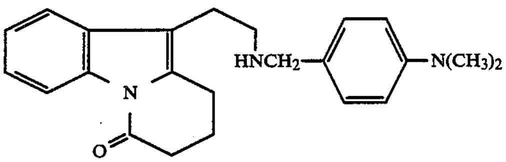

7 g (26 mmoles) Compound D4 and 3.4 g 4-dimethylaminobenzaldehyde treated by the process of Example 3 produced after recrystallisation in ethanol, 4 g white crystals E7, of m. pt. 188°-190° C.

IR (KBr)ν=3100-2200; 1710; 1700; 770; 760 $cm^{-1}$.

UV($CH_3OH$)λmax=242; 265; 292; 302 nm.

M.S. empirical formula $C_{23}H_{27}N_3O$.

M.W. found: 361.2160; theory: 361.2154.

m/e (% relative intensity) 361 (M+25); 228 (7); 199 (43); 170 (28); 161 (46); 134 (100).

EXAMPLE 8

6-Oxo-10-[2-(3-methoxybenzyl)aminoethyl]6,7,8,9-tetrahydropyrido[1,2-a]indole hydrochloride (E8)

(E8)

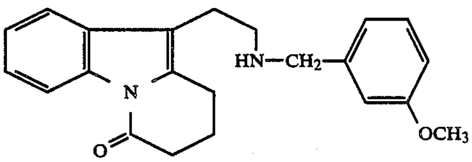

8 g (30 mmoles) Compound D4, 4.6 g (33 mmoles) meta-anisaldehyde, 1.15 g (18 mmoles) $NaBH_3CN$ and 0.6 g (1.5 mmoles) aliquat 336 were dissolved in 400 ml of a 5:2 mixture of methylene chloride and methanol and stirred for 24 hours at room temperature. The mixture was concentrated, the residue was taken up in methylene chloride and washed with 100 ml water. The organic solution was dried over magnesium sulphate and concentrated.

The residue was taken up in dry acetone and acidified with ethanolic hydrochloric acid producing, after recrystallisation in acetone, 3 g white crystals of E8, m.pt.=125° C.

IR(KBr)ν=3100-2300; 1700; 790; 770; 740; 690 $cm^{-1}$.

UV($CH_3OH$)λmax=210; 242; 266; 272; 292; 302 nm.

Mass spectroscopy empirical formula: $C_{22}H_{24}H_2O_2$

Molecular weight found: 348.1839; theory: 348.1837. m/e (% relative intensity) 348 (M+, 2.5); 199 (42); 170 (10); 150 (62); 121 (100).

EXAMPLES 9 TO 12

The following compounds were prepared analogously:

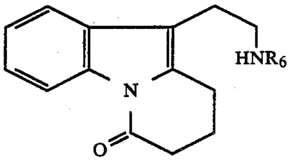

| Example No | $R_6$ |
|---|---|
| (E9) | 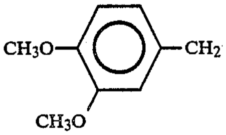 |
| (E10) | 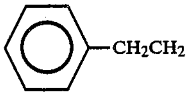 |
| (E11) | 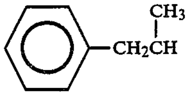 |
| (E12) | 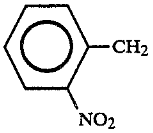 |

6-Oxo-10-[2-(3,4-dimethoxybenzyl)aminoethyl]-6,7,8,9-tetrahydropyrido[1,2-a]indole hydrochloride (E9)

m. pt.=126°-136° C.

IR(KBr)ν=3100-2400; 1700; 770; 760 $cm^{-1}$.

UV($CH_3OH$)λmax=208; 242; 264; 292; 302 nm.

M.S. empirical formula: $C_{23}H_{26}N_2O_3$

M.W. found: 378.1944; theory: 378.1943.

m/e (% relative intensity) 378, (M+, 15); 376 (22); 199 (92); 179 (100); 152 (92).

6-Oxo-10-[2-(2-phenylethyl)aminoethyl]-6,7,8,9-tetrahydropyrido[1,2-a]indole hydrochloride (E10)

m. pt.=219°-221° C.

IR(KBr)ν=3100-2400; 1705; 770-760; 700 $cm^{-1}$.

UV($CH_3OH$)λ=242; 266; 292; 302 nm.
M.S. empirical formula: $C_{22}H_{24}N_2O$
M.W. found: 332.1890; theory: 332.1888.
m/e (% relative intensity): 332(M+, 8); 241(3); 212(5); 199(39); 134(100); 105(58).

6-Oxo-10-[2-(1-methyl-2-phenylethyl)aminoethyl]-6,7,8,9-tetrahydropyrido[1,2-a]indole hydrochloride (E11)

m. pt.=208°-210° C.
IR(KBr)ν=3100-2500; 1710; 750; 700 $cm^{-1}$.
UV($CH_3OH$)λmax=242; 266; 292; 302 nm.
M.S. empirical formula: $C_{23}H_{26}N_{20}$.
M.W. found: 346.2042; theory: 346.2045.
m/e (% relative intensity): 346(M+, 6) 255(25); 148(100); 119(41); 91(44).

6-Oxo-10-[2-(2-nitrobenzyl)aminoethyl]-6,7,8,9-tetrahydropyrido[1,2-a]indole hydrochloride (E12)

m.pt.=206° C.
IR(KBr)ν=3100-2300; 1710; 760; 750; 700 $cm^{-1}$.
UV($CH_3OH$)λmax=211, 242; 263; 292; 302 nm.
M.S. empirical formula: $C_{21}H_{21}N_3O_3$
M.W. found: 363.1582; theory: 363.15828
m/e (% relative intensity): 363(M;, 2); 331(2); 328(5); 214(7); 211(15); 199(68); 170(31); 165(100); 156(83); 106(15).

EXAMPLE 13

6-Oxo-10-[2-(4-aminobenzyl)aminoethyl]-6,7,8,9-tetrahydropyrido[1,2-a]indole dihydrochloride (E13)

E13

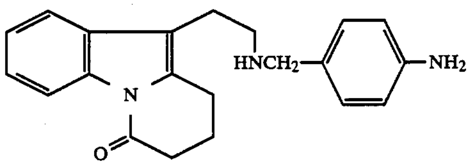

7.3 g Compound D15 was hydrogenated at atmospheric pressure and room temperature in solution in 200 ml ethanol in the presence of Raney nickel. After filtration on Clarsel and acidification with ethanol/HCl, 5.3 g bright yellow crystals of E13 were obtained.

m. pt.=210°-215° C.
IR(KBr)ν=3200-2300; 1715; 770; 750 $cm^{-1}$.
UV($CH_3OH$)λmax=207; 243; 275; 290; 302 nm.
M.S. empirical formula: $C_{21}H_{23}N_3O$.
M.W. found: 333.1835; theory: 333.1841
m/e (% relative intensity): 333(M+, 5); 228(23); 199(92); 170(44); 144(19); 143(25); 108(100).

EXAMPLES 14 AND 15

The following compounds were prepared analogously:

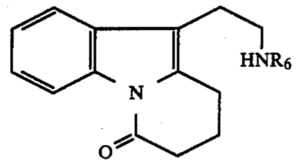

| Example No. | $R_6$ |
| --- | --- |
| 14 | 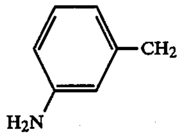 |
| 15 | 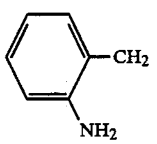 |

6-Oxo-10-[2-(3-aminobenzyl)aminoethyl]-6,7,8,9-tetrahydropyrido[1,2-a]indole dihydrochloride (E14)

m.pt.=205°-210° C.
IR(KBr)ν=3200-2300; 1710; 770; 750; 745; 690 $cm^{-1}$.
UV($CH_3OH$)λmax=210; 242; 270; 292; 302 nm.
M.S. empirical formula: $C_{21}H_{23}N_3O$.
M.W. found: 333.1852; theory: 333.1841.
m/e (% relative intensity): 333(M+, 3); 199(27); 170(7); 135(56); 106(100).

6-Oxo-10[2-(2-aminobenzyl)aminoethyl]-6,7,8,9-tetrahydropyrido[1,2-a]indole dihydrochloride (E15)

m. pt.=190° C.
IR(KBr)ν=3200-2200; 1680; 780; 760 $cm^{-1}$.
UV($CH_3OH$)λmax=209; 241; 265; 292; 302 nm.
M.S. empirical formula: $C_{21}H_{23}N_3O$.
M.W. found: 333.1846; theory: 333.1841.
m/e (% relative intensity): 333(M+, 1); 199(9); 170(10); 135(29); 106(100).

EXAMPLE 16

6-Oxo-10-[2-(3-pyridylmethyl)aminoethyl]-6,7,8,9-tetrahydropyrido[1,2-a]indole dihydrochloride (E16)

E16

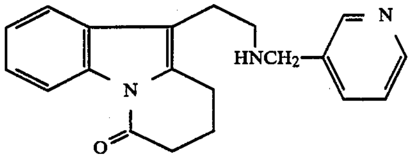

7 g Compound D4 and 3.5 g pyridine-3-aldehyde treated by the process of Example 3 gave 3.5 g beige crystals of E16.

m. pt.=263°-266° C. (decomposition)
IR(KBr)ν=3100-2300; 2090; 1990; 1700; 750; 740; 690 $cm^{-1}$.
UV($CH_3OH$)λmax=210; 242; 260; 265; 292; 300 nm.
M.S. empirical formula: $C_{20}H_{21}N_3O$
M.W. found 319.1683; theory: 319.16845 m/e (% relative intensity): 319(M+, 6); 199(62.5) 170(19); 144(4); 121(100); 92(94).

EXAMPLE 17

6-Oxo-10-[2-(1-methyl-4-piperidyl)aminoethyl]-6,7,8,9-tetrahydropyrido[1,2-a]indole dihydrochloride (E17)

E17

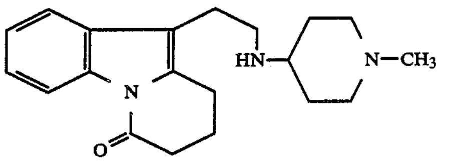

8 g Compound D4 and 4 g 1-methyl-4-piperidone treated by the process of Example 8 gave 6 g bright green crystals.

m. pt.=306°-310° C. (decomposition)

IR(KBr)ν=3100-2300; 1705; 770; 755 cm$^{-1}$.

UV(CH$_3$OH)λmax=207; 242; 265; 292; 302 nm.

M.S. empirical formula: $C_{20}H_{27}N_3O$.

M.W. found: 325.2147; theory: 325.2154.

m/e (% relative intensity): 325(M+, 2); 199(3); 127(90); 198(18); 196(30); 84(25); 70(100).

EXAMPLE 18

6-Oxo-10-[2-(1-thienylmethyl)aminoethyl]-6,7,8,9-tetrahydropyrido[1,2-a]indole hydrochloride (E18)

E18

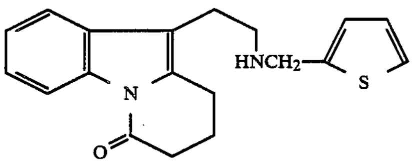

16 g Compound D4 and 9 g thiophene-2-aldehyde treated by the process of Example 8 gave 5 g cream crystals of E18.

m. pt.=232° C.

IR(KBr)ν=3000-2300; 1705; 755; 740 cm$^{-1}$.

UV(CH$_3$OH)λmax=206; 240; 292; 302 nm.

M.S. empirical formula: $C_{19}H_{20}N_2OS$.

M.W. found: 324.1303; theory: 324.1296.

m/e (% relative intensity): 324(M+, 3.3); 199(53); 170(15); 126(40); 97(100).

EXAMPLE 19

10-(2-Aminoethyl)-6,7,8,9-tetrahydropyrido[1,2-a]indole hydrochloride (E19)

E19

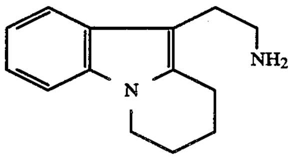

15 g Compound D4 was added in small fractions to a suspension of 17 g $AlCl_3$ and 7 g $LiAlH_4$ in 150 dry ether and 150 ml tetrahydrofuran. It was left for 1 hour at room temperature, then the excess hydride was destroyed with water and sodium hydroxide. It was filtered on Clarsel, concentrated, taken up in $CH_2Cl_2$, the solution washed with water, dried and acidified with ethanol/HCl, giving 10 g white crystals of E19.

m. pt.=288°-290° C.

IR(KBr)ν=3300-2400; 740 cm$^{-1}$.

UV(CH$_3$OH)λmax=240; 285; 296 nm.

M.S. empirical formula: $C_{14}H_{18}N_2$.

M.W. found: 214.1469; theory: 214.1469.

m/e (% relative intensity): 214(M+, 18); 184(100); 156(11).

EXAMPLE 20

10-[2-(4-Dimethylaminobenzyl)aminoethyl]-6,7,8,9-tetrahydropyrido[1,2-a]indole dihydrochloride (E20)

E20

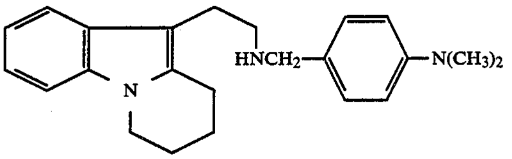

7.5 g Compound E7 was subjected to the process of Example 19 and gave 7.1 g of white crystals of E20.

m. pt.=190° C.

IR(KBr)ν=3100-2300; 740 cm$^{-1}$.

UV(CH$_3$OH)λmax=215; 228; 267; 295 nm.

M.S. empirical formula: $C_{23}H_{29}N_3$.

M.W. found: 347.2356; theory: 347.2361.

m/e (% relative intensity): 347(M+, 10); 345(2.5); 214(2.5); 189(85) 162(12); 156(10); 134(100).

EXAMPLE 21

10-[2-Benzylaminoethyl]-6,7,8,9-tetrahydropyrido[1,2-a]indole hydrochloride (E21)

E21

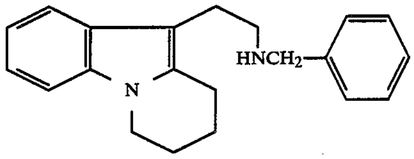

Method 1

5.5 g Compound D14 was subjected to the process of Example 19 and gave 5 g of white crystals of E21.

m. pt.=203° C.

IR(KBr)ν=3100-2300; 750-740; 700 cm$^{-1}$.

UV(CH$_3$OH)λ max=214; 228; 260; 285; 295 nm.

M.S. empirical formula: $C_{21}H_{24}N_2$.

M.W. found: 304.1938; theory: 304.1939.

m/e (% relative intensity): 304(M+, 5); 185(100); 184(81); 196(11); 120(7); 91(24).

Method 2

The amide D16 was reduced by the process of Example 19 and produced the expected compound E21.

EXAMPLE 22

2-Methyl-10-(2-benzylaminoethyl)-6,7,8,9-tetrahydropyrido[1,2-a]indole hydrochloride (E22)

E22

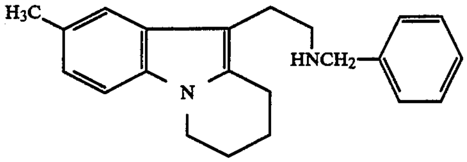

10 g Compound D19 were reduced as described in Example 19 to produce 6 g white crystals of E22.

m. pt.=226° C.

IR(KBr)ν=3100–2300; 790; 750; 700 $cm^{-1}$.

UV($CH_3OH$)λ max=212; 232; 280; 290; 300 nm.

M.S. empirical formula: $C_{22}H_{26}N_2$.

M.W. found: 318.2095; theory: 318.2096.

m/e (% relative intensity): 318(M+, 8); 199(100); 198(100); 170(11); 120(5); 91(19).

EXAMPLE 23

10-(2-Aminoethyl)-5a,6,7,8,9,10-hexahydropyrido[1,2-a]indole dihydrochloride (E23)

E23

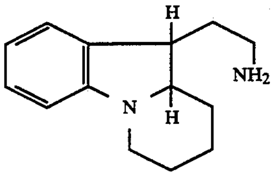

To 6 g of the compound D4 in solution, in 50 ml dimethylsuphoxide was added 2 g $NaBH_4$ then fraction by fraction, a solution of 5 ml methane sulphonic acid in 25 ml dimethylsulphoxide. Leaving overnight at room temperature, neutralising with sodium hydroxide, extracting and acidifying gave 3 g white crystals of E23.

m.pt.=210° C.

IR(KBr)ν=3300–2400; 735 $cm^{-1}$.

UV($CH_3OH$)λ max=213; 256; 302 nm,

M.S. empirical formula: $C_{14}H_{20}N_2$.

M.W. found: 216.1625; theory: 216.16264.

m/e (% relative intensity): 216(M+, 24); 214(18); 198(6); 184(100); 172(42); 156(13) 144(6); 143(6); 130(13).

EXAMPLE 24

10-[2-(3-Dimethylaminobenzyl)aminoethyl]-6,7,8,9 tetrahydropyrido[1,2-a]indole dihydrochloride (E24)

E24

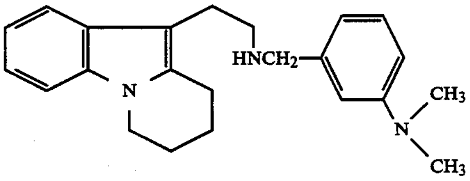

The Compound D17 was reduced by the process of Example 19, giving 6.8 g white crystals of E24, m.pt. 208° C.

IR(KBr)ν=3100–2300; 790; 750; 690 $cm^{-1}$.

UV($CH_3OH$)λ max=232; 262; 284; 295 nm.

M.S. empirical formula: $C_{23}H_{29}N_3$.

M.W. found: 347.2357; theory: 347.2361.

m/e (% relative intensity): 347(M+, 1); 345(7); 185(59); 184(100); 156(12); 151(21); 150(24); 134(24).

EXAMPLE 25

10-(2-Benzylaminoethyl)-5a,6,7,8,9,10-hexahydropyrido[1,2-a]indole dihydrochloride (E25)

E25

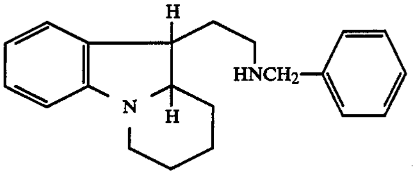

10 g $KBH_4$ and the, dropwise, 12 ml methane sulphonic acid was added to 9.4 g compound E 21 dissolved in 90 ml nitromethane. One hour after completion of this addition neutralising cautiously, extracting and acidifying gave 10 g white crystals of E25.

m.pt=140°–145° C.

IR(KBr)ν=3100–2200; 750; 700 $cm^{-1}$.

UV($CH_3OH$)λ max=216; 257; 302 nm.

M.S. empirical formula: $C_{21}H_{26}N_2$.

M.W. found: 306.2102 theory: 306.2095.

m/e (% relative intensity): 306(M+, 22); 198(29); 185(37); 184(46); 172(48); 171(44); 135(26); 107(100).

EXAMPLE 26

10-[2-(4-Ethylaminobenzyl)aminoethyl]-6,7,8,9-tetrahydropyrido-[1,2-a]indole dihydrochloride (E26)

E26

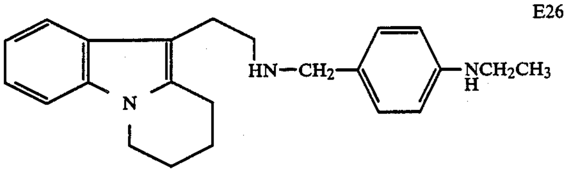

7.2 g Compound D18, reduced by the process of Example 19 gave 6 g yellow crystals of E26.

m.pt.=222° C.

IR(KBr)ν=3100–2300; 800; 760; 730 $cm^{-1}$.

UV($CH_3OH$)λ max=212; 230; 262; 284; 292 nm.

M.S. empirical formula $C_{23}H_{29}N_3$.

M.W. found: 347.2354; theory; 347.2361.

m/e (% relative intensity): 347(M+, 2); 345(2); 214(9); 285(71); 284(100); 156(12); 134(36).

EXAMPLE 27

10-[2-(3-Aminobenzyl)aminoethyl]-6,7,8,9-tetrahydropyrido[1,2-a]indole dihydrochloride (E27)

E27

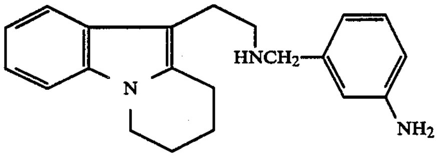

10 g Compound D5 reduced with 8 g $LiAlH_4$ and 20 g $AlCl_3$ in 500 ml tetrahydrofuran produced after treatment by the process of Example 19, 5 g of bright maroon crystals of E27.

m.pt.=220°-230° C. (decomposition).

IR(KBr)ν=3200-2300; 790; 740; 690 $cm_{-1}$.

UV($CH_3OH$)λ max=214; 230; 284; 292 nm.

M.S. empirical formula $C_{21}H_{25}N_3$.

M.W. found: 319.2025; theory: 319.2048.

m/e(% relative intensity): 319(M+, 3); 185(100); 184(68); 156(11); 135(6); 106(24).

EXAMPLE 28

6-Oxo-10-[2-(3,4-Methylenedioxybenzyl)aminoethyl]-6,7,8,9-tetrahydropyrido[1,2-a]indole hydrochloride (E28)

E28

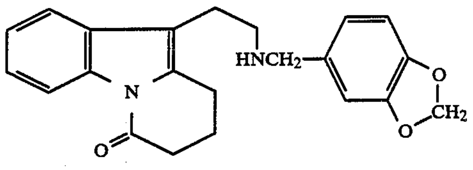

10 g Compound D4 and 6.5 g piperonal treated by the process of Description 15 gave 5.5 g steely blue crystals of E28.

m.pt.=129°-130° C.

IR(KBr)ν=3100-2400; 1710; 800; 770; 750; 630 $cm^{-1}$.

UV($CH_3OH$)λ max=212; 242; 270; 290 nm.

M.S. empirical formula: $C_{22}H_{22}N_2O_3$.

M.W. found: 362.1624; theory: 362.1630.

m/e(% relative intensity): 362(M+, 3); 360(3); 199(30); 170(12); 164(17); 143(5); 136(100).

EXAMPLE 29

10-[2-(3,4-Methylenedioxybenzyl)aminoethyl]-6,7,8,9-tetrahydropyrido[1,2-a]indole hydrochloride (E29)

(E29)

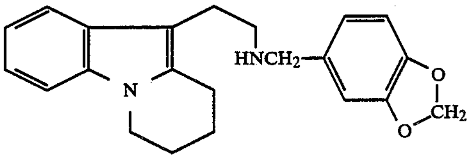

4 g Compound E28 reduced by the process of Example 19 gave 3 g white crystals of E29.

m.pt.=196° C.

IR(KBr)ν=3100-2300; 810; 740 $cm^{-1}$.

UV($CH_3OH$)λ max=213; 228; 288; 294 nm.

M.S. empirical formula: $C_{22}H_{24}N_2O_2$.

M.W. found: 348.1842, theory: 348.1837.

m/e(% relative intensity): 348 (M+, 3.5); 346(2); 298(3.5); 185(100); 184(81); 156(12); 135(38).

EXAMPLE 30

6-Oxo-10-[2-(2-nitrophenyl)aminoethyl]-6,7,8,9-tetrahydropyrido[1,2-a]indole hydrochloride (E30)

E30

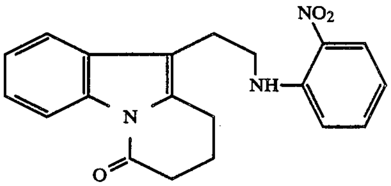

13 g Compound D4 and 7 g 1-fluoro-2-nitrobenzene were heated under reflux in 100 ml pyridine for 16 hours. The mixture was then cooled to room temperature and 10 ml 10N ammonium hydroxide was added and the mixture concentrated to dryness. The residue was slurried in 100 ml ethanol, filtered off and the precipitate washed with 100 ml water, thus giving 14 g crystals of E30, melting-point 170° C.

EXAMPLE 31

6-Oxo-10-[2-(4-aminophenyl)aminoethyl]-6,7,8,9-tetrahydropyrido[1,2-a]indole hydrochloride (E31)

E31

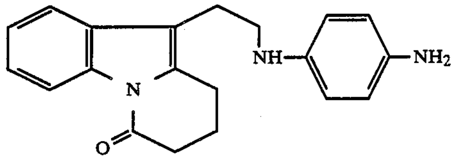

10 g Compound D7 were reduced in 100 ml dimethylformamide (DMF) with 15 ml ethanol/HCl and 1 g Raney nickel at 50° C. under 50 bars of hydrogen in 16 hours. 8.5 g crystals of E32 were obtained after working-up.

m.pt=180° C.

IR(KBr)ν=3300-2400; 1700; 1650; 1620; 750 $cm^{-1}$.

M.S. empirical formula: $C_{20}H_{21}N_3O$.

M.W. found: 319.1690; theory 319.1684.

m/e(% relative intensity): 319(M.+,12.5); 199(9.4); 144(11); 121(100); 108(26).

EXAMPLE 32

6-Oxo-10-[2-(2-aminophenyl)aminoethyl]-6,7,8,9-tetrahydropyrido[1,2-a]indole hydrochloride (E32)

E32

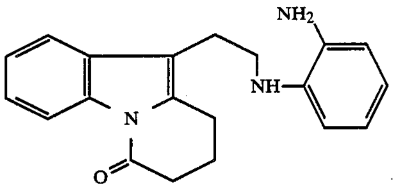

10 g Nitro-derivative E30 were reduced in 100 ml DMF plus 15 ml ethanol/HCl in the presence of 1 g Raney nickel at 50° C. under 50 atmospheres of hydrogen in 16 hours. 8 g white crystals of the hydrochloride E32 were obtained after working-up.

m.pt=225° C.

IR(KBr)ν=3400; 3000-2400; 1700; 1620; 750 $cm^{-1}$.

M.S. empirical formula; $C_{20}H_{21}N_3O$.

M.W. found: 319.1690; theory; 319.168452.

m/e(% relative intensity): 319(M.+, 23); 199(19); 121(100); 94(18).

EXAMPLE 33

10-[2-(4-Aminophenyl)aminoethyl]-6,7,8 9-tetrahydropyrido[1,2-a]indole dihydrochloride (E33)

E33

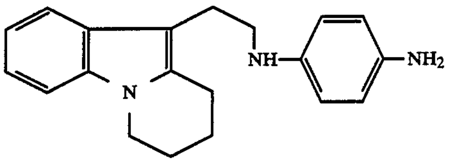

8 g Compound E31 were added slowly to a solution of 3 g $LiAlH_4$ and 8 g $AlCl_3$ in 300 ml ether. After 24 hours heating under reflux, the reaction being incomplete, the same volume of reducing-mixture was added and again heated under reflux for 24 hours. After treatment the base was acidified with ethanolic hydrochloric acid and the salt recrystallised in acetone, giving 1.8 g of crystals E33.

m.pt=206° C.

IR (KBr)ν=3420; 3100–2400; 1510; 1460; 730 $cm^{-1}$.

EXAMPLE 34

10-[2-(2-Aminophenyl)aminoethyl)-6,7,8,9-tetrahydropyrido[1,2-a]indole dihydrochloride (E34)

E34

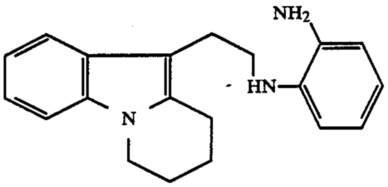

17.3 g Compound E32 were added slowly to a solution of 7 g $LiAlH_4$ and 17 g $AlCl_3$ in 300 ml tetrahydrofuran. The mixture was heated under reflux for 24 hours, then treated. The base was acidified in methanol, giving 4.8 g hydrochloride E34.

m.pt=218° C.

IR (KBr)ν=3410; 3000–2400; 1610; 1500; 1460; 730 $cm^{-1}$.

EXAMPLE 35

10-[2-(3-Pivalylaminobenzyl)aminoethyl]-6,7,8,9-tetrahydropyrido[1,2-a]indole dihydrochloride (E35)

E35

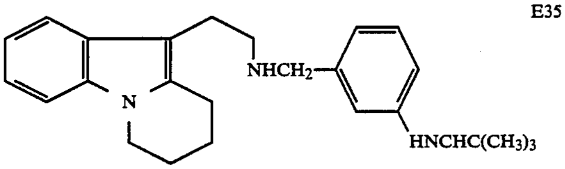

6.5 g Compound D8 were reduced with a mixture of $LiAlH_4$ (3.3 g), $AlCl_3$(7.4 g) and ether (200 ml). After working up and acidification with EtOH/HCl the hydrochloride was crystallised from ethyl acetate giving 4.5 g crystals of E35.

m.pt=224° C.

IR(KBr)ν=3400; 3100–2400; 1560; 1460; 730 $cm^{-1}$.

UV($CH_3OH$)λmax=230; 257; 286; 294 nm.

M.S. empirical formula: $C_{26}H_{35}N_3$.

m/e(% relative intensity): 389(M+5); 186(15); 185(100); 184(51); 176(15); 156(6).

EXAMPLE 36

10-[2-(3-Ethylaminobenzyl)aminoethyl]-6,7,8 9-tetrahydropyrido[1,2-a]indole dihydrochloride (E36)

E36

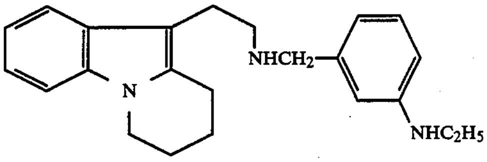

10 g Compound D9 were reduced by the method of Example 35, then acidified and recrystallised in a 4/1 acetone/ethanol mixture, giving 3.9 g hydrochloride E36.

m.pt=218° C.

IR(KBr)ν=3500; 3100–2400; 1560; 1450; 740 $cm^{-1}$.

UV($CH_3OH$)λmax=230; 256; 286; 293 nm.

M.S. empirical formula: $C_{23}H_{29}N_3$.

M.W found: 347.2356; theory; 347.23613.

m/e(% relative intensity): 347(M+, 4); 186(15); 185(100); 184(49); 134(36).

EXAMPLE 37

10-[2-(3-Piperidinobenzyl)aminoethyl]-6,7,8,9-tetrahydropyrido[1,2-a]indole tri-hydrochloride (E37)

E37

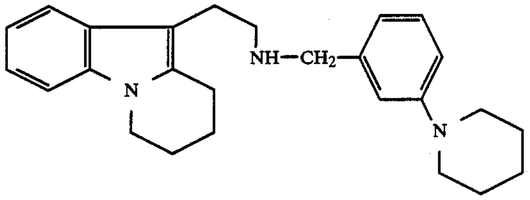

8 g Compound D10 were reduced by the method of Example 35, acidified, and the hydrochloride washed with ethyl acetate to give 6.5 g crystals of E37.

IR(KBr)ν=3400; 3100–2400; 1600; 1460; 740 $cm^{-1}$.

UV($CH_3OH$)λmax=228; 265; 294 nm.

M.S. empirical formula: $C_{26}H_{33}N_3$.

M.W found: 387.2663; theory: 387.267433.

m/e(% relative intensity): 387(M+7); 202(53); 185(100); 184(55); 174(41).

EXAMPLE 38

10-[2-(3-Diisopropylaminobenzyl)aminoethyl]-6,7,8 9-tetrahydropyrido[1,2-a]indole trihydrochloride (E38)

E38

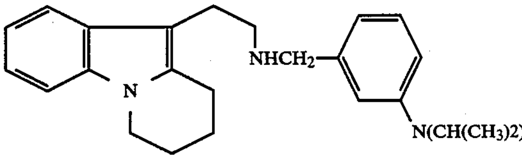

4.5 g Compound D11 were reduced by the method of Example 35. Acidification gave 3.9 g of hydrochloride E38.

m.pt=180° C.

IR(KBr)ν=3400; 3100–2400; 1600; 1460; 740 $cm^{-1}$.

UV($CH_3OH$)λmax=229; 258; 295; nm.

EXAMPLE 39

10-[2-(3-Methylaminobenzyl)aminoethyl]-6,7,8,9-tetrahydropyrido[1,2-a]indole trihydrochloride (E39)

E39

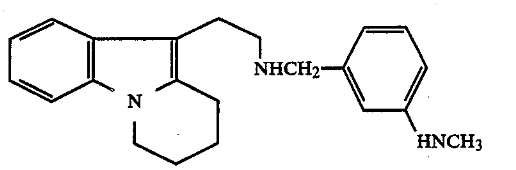

7.9 g Compound D12 were reduced by the method of Example 35. Acidification in ethyl acetate gave 4.7 g hydrochloride E39.

m.pt=204° C.

IR(KBr)$\nu$=3400; 3100–2400; 1600; 1460; 745 $cm^{-1}$.

UV($CH_3OH$)$\lambda$max=228; 256; 288: 293 nm.

M.S. empirical formula: $C_{22}H_{27}N_3$.

M.W found: 333.2193; theory: 333.220486.

m/e(% relative intensity): 333(M+6); 190(16); 189(100); 188(55); 156(8); 120(30).

EXAMPLE 40

10-[2-(3-Pyrrolidinobenzyl)aminoethyl]-6,7,8,9-tetrahydropyrido[1,2-a]indole trihydrochloride (E40)

E40

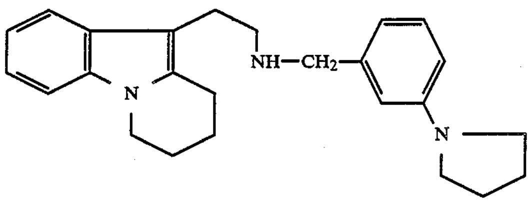

8.4 g Compound D13 were reduced by the method of Example 35 and acidified in ethyl acetate, giving 6.4 g hydrochloride E40.

m.pt=134°-138° C.

IR(KBr)$\nu$=3400; 3100–2400; 1600; 740 $cm^{-1}$.

UV($CH_3OH$)$\lambda$max=228; 255; 293 nm.

The following compounds are prepared analogously:

10-[2-(3-Diethylaminobenzyl)aminoethyl]-6,7,8,9-tetrahydropyrido[1,2-a]indole dihydrochloride (E41) E41

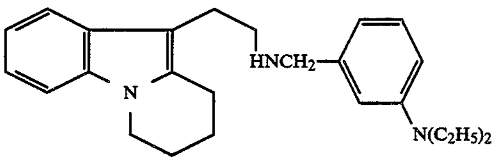

10-[2-(4-Diethylaminobenzyl)aminoethyl]-6,7,8,9-tetrahydropyrido[1,2-a]indole dihydrochloride (E42) E42

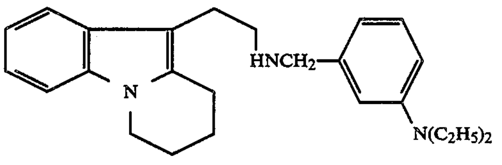

PHARMACOLOGICAL DATA

Triethyltin-induced cerebral oedema in the rat.

The cerebral oedema is induced by oral administrations repeated for 5 consecutive days—one administration per day—of triethyltin chloride at a dose of 2 mg/kg. The study substances are also administered orally twice daily as aqueous solution or suspension at a dose of 1 ml/100 g body-weight; these administrations are given during the 5 days of intoxication with tin. Three groups of 10 male specific pathogen-free (SPF) Wistar rats of 280±10 g body-weight are used for each compound studied:

1 control group 1 group intoxicated with triethyltin 1 group intoxicated with triethyltin and treated with the studied compound.

The rats are sacrificed on the evening of the fifth day; the brain is removed, weighed fresh and after desiccation to constant weight and the water content of each brain is calculated:

$$[H_2O] = \text{fresh weight} - \text{dry weight.}$$

The following are then calculated:

the mean water content (M±Sm%) of each group;

the protection index P due to the administered compound:

$$P\% = 1 - \frac{[H_2O]\text{treated group} - [H_2O]\text{control group}}{[H_2O]\text{triethyltin group} - [H_2O]\text{control group}} \times 100$$

The significance is evaluated:

by the Student t-test; *P<0.001, P<0.01. *P<0.05.

or by the Darmois t'-test: Δ=significant.

The results obtained are summarised in Table 1.

Toxicity

No toxic effects were observed in the above tests.

TABLE 1

| Compound No. | Triethyltin-induced cerebral oedema % protection at a dose administered (mg. kg$^{-1}$ p.o.) 2 × 50 | 2 × 25 | 2 × 12.5 |
|---|---|---|---|
| D4 | | −21** | |
| D14 | −65*** | | |
| E1 | −51** | | |
| E2 | −40*** | | |
| E3 | −40Δ | | |
| E4 | −26* | | |
| E5 | −47*** | | |
| E6 | −24* | | |
| E7 | −77*** | −28*** | |
| E8 | −50** | | |
| E9 | −68Δ | | |
| E10 | −22* | | |
| E11 | −49*** | | |
| E12 | −28Δ | | |
| E13 | −49Δ | | |
| E14 | −65Δ | | |
| E15 | −25Δ | | |
| E16 | −53*** | | |
| E17 | −41*** | | |
| E18 | −49Δ | | |
| E19 | | −34** | |
| E20 | −94*** | −72*** | −49** |
| E21 | −88*** | −42*** | |
| E22 | −51*** | | |
| E23 | −46*** | | |
| E24 | −99*** | −82*** | −67*** |

TABLE 1-continued

| Compound No. | Triethyltin-induced cerebral oedema % protection at a dose administered (mg. $kg^{-1}$ p.o.) 2 × 50 | 2 × 25 | 2 × 12.5 |
|---|---|---|---|
| E25 | −45Δ | | |
| E26 | −96*** | | −63Δ |
| E27 | −69*** | | |
| E29 | −64*** | | |
| E33 | −18* | | |
| E36 | | | −43Δ |
| E38 | | | −28* |
| E39 | | | −40*** |
| E40 | | | −19* |

We claim:

1. A compound of formula (I) or a pharmaceutically acceptable salt thereof:

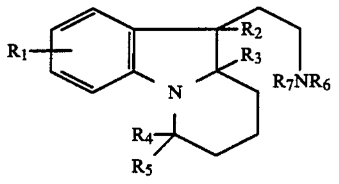
(I)

wherein $R_1$ is hydrogen, $C_{1-6}$ alkyl, $C_{1-6}$ alkoxy or halogen;

$R_2$ and $R_3$ are both hydrogen or together represent a bond;

$R_4$ is hydrogen and $R_5$ is hydrogen or $R_4$ and $R_5$ together represent an oxo group;

$R_6$ is hydrogen; $C_{1-6}$ alkyl; $C_{3-7}$ cycloalkyl; $C_{3-7}$ cycloalkyl-$C_{1-4}$ alkyl; phenyl or phenyl $C_{1-7}$ alkyl in which the phenyl moiety is optionally substituted by one or two of halogen, ortho-nitro, meta- or para-methoxy, methyl or $NR_8R_9$ wherein $R_8$ and $R_9$ are independently hydrogen or $C_{1-6}$ alkyl or $R_8$ and $R_9$ together form polymethylene of 2 to 6 carbon atoms, or the phenyl moiety is 3,4-disubstituted by methylenedioxy or ethylendioxy; heteroaryl-$C_{1-4}$ alkyl, wherein said heteroaryl moiety is pyridyl, thienyl, furyl or optionally N-methyl substituted pyrryl; or aliphatic heterocyclyl or aliphatic heterocyclyl-$C_{1-4}$ alkyl, wherein said aliphatic heterocyclyl moiety is optionally N-methyl substituted piperidyl or optionally N-methyl substituted pyrrolidinyl; and $R_7$ is hydrogen or $C_{1-4}$ alkyl;

with the proviso that when $R_1$ is hydrogen, $R_2$ and $R_3$ are a bond, $R_4$ and $R_5$ are an oxo group and $R_7$ is hydrogen, $R_6$ is other than hydrogen or benzyl.

2. A compound of formula (II) or a pharmaceutically acceptable salt thereof:

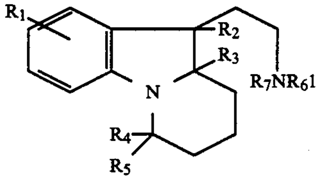
(II)

wherein $R_1$ is hydrogen, $C_{1-6}$ alkyl, $C_{1-6}$ alkoxy or halogen;

$R_2$ and $R_3$ are both hydrogen or together represent a bond;

$R_4$ is hydrogen and $R_5$ is hydrogen or $R_4$ and $R_5$ together represent an oxo group;

$R_6{}^1$ is hydrogen, $C_{1-4}$ alkyl, $C_{5-7}$ cycloalkyl, or phenyl-$C_{1-7}$ alkyl optionally monosubstituted by fluoro, chloro, bromo, methoxy, nitro or $NR_8R_9$ where $R_8$ and $R_9$ are independently hydrogen or $C_{1-6}$ alkyl or $R_8$ and $R_9$ together are $C_{2-6}$ polymethylene; and $R_7$ is hydrogen or $C_{1-4}$ alkyl;

with the proviso that when $R_1$ is hydrogen, $R_2$ and $R_3$ are a bond, $R_4$ and $R_5$ are an oxo group and $R_7$ is hydrogen, $R_6{}^1$ is other than hydrogen or benzyl.

3. A compound according to claim 2, wherein $R_4$ and $R_5$ are hydrogen.

4. A compound according to claim 3, wherein $R_6{}^1$ is phenyl $C_{1-4}$ alkyl optionally substituted by said $NR_8R_9$.

5. A compound according to claim 1, wherein $R_6$ is benzyl or 1-methyl-2-phenylethyl, optionally monosubstituted in the phenyl moiety by $NR_8R_9$.

6. A compound according to claim 5, wherein $R_6$ is benzyl or 1-methyl-2-phenylethyl meta- or para-substituted by amino optionally substituted by one or two methyl or ethyl groups.

7. A compound according to claim 6, wherein $R_7$ is hydrogen.

8. A compound according to claim 7, wherein $R_1$ is hydrogen.

9. A compound according to claim 4, wherein $R_2$ and $R_3$ represent a bond.

10. A compound according to claim 9, wherein $R_6{}^1$ is benzyl or 1-methyl-2-phenylethyl, optionally monosubstituted in the phenyl moiety by $NR_8R_9$.

11. A compound according to claim 10, wherein $R_6{}^1$ is benzyl or 1-methyl-2-phenylethyl meta- or para-substituted by amino optionally substituted by one or two methyl or ethyl groups.

12. A compound according to claim 11 wherein $R_7$ is hydrogen.

13. A compound according to claim 9, wherein $R_1$ is hydrogen.

14. 10-[2-(4-Dimethylaminobenzyl)aminoethyl]-6,7,8,9-tetrahydropyrido[1,2-a]indole, 10-[2-(3-Dimethylaminobenzyl)aminoethyl]-6,7,8,9-tetrahydropyrido[1,2-a]indole, 10-[2-(4-Ethylaminobenzyl)aminoethyl]-6,7,8,9-tetrahydropyrido-[1,2-a]indole, 10-[2-(3-Ethylaminobenzyl)aminoethyl]-6,7,8 9-tetrahydropyrido[1,2-a]indole, or 10-[2-(3-Methylaminobenzyl)aminoethyl]-6,7,8,9-tetrahydropyrido[1,2-a]indole, or a pharmaceutically acceptable salt thereof.

15. 2-Methyl-6-oxo-10-(2-aminoethyl)-6,7,8,9-tetrahydropyrido[1,2-a]indole,

6-Oxo-10-(2-isopropylaminoethyl)-6,7,8,9-tetrahydropyrido[1,2-a]indole,

6-Oxo-10-(2-cyclopentylaminoethyl)-6,7,8,9-tetrahydropyrido[1,2-a]indole,

6-Oxo-10-[2-(cyclohexylmethyl)aminoethyl]-6,7,8,9-tetrahydropyrido[1,2-a]indole, 6-Oxo-10-[2-(4-fluorobenzyl)aminoethyl]-6,7,8,9-tetrahydropyrido[1,2-a]indole, 6-Oxo-10-[2-(4-chlorobenzyl)aminoethyl]-6,7,8,9-tetrahydropyrido[1,2-a]indole, 6-Oxo-10-[2-(4-dimethylaminobenzyl)aminoethyl]-6,7,8,9-tetrahydropyrido[1,2-a]indole, 6-Oxo-10-[2-(3-methoxybenzyl)aminoethyl]-6,7,8,9-tetrahydropyrido[1,2-a]indole,
6-Oxo-10-[2-(3,4-dimethoxybenzyl)aminoethyl]-6,7,8,9-tetrahydropyrido[1,2-a]indole,
6-Oxo-10-[2-(2-phenylethyl)aminoethyl]-6,7,8,9-tetrahydropyrido[1,2-a]indole,
6-Oxo-10-[2-(1-methyl-2-phenylethyl)aminoethyl]-6,7,8,9-tetrahydropyrido[1,2-a]indole,
6-Oxo-10-[2-(2-nitrobenzyl)aminoethyl]-6,7,8,9-tetrahydropyrido[1,2-a]indole,
6-Oxo-10-[2-(4-aminobenzyl)aminoethyl]-6,7,8,9-tetrahydropyrido[1,2-a]indole dihydrochloride,
6-Oxo-10-[2-(3-aminobenzyl)aminoethyl)-6,7,8,9-tetrahydropyrido[1,2-a]indole dihydrochloride,
6-Oxo-10-[2-(2-aminobenzyl)aminoethyl]-6,7,8,9, tetrahydropyrido[1,2-a]indole dihydrochloride,
6-Oxo-10-[2-(3-pyridylmethyl)aminoethyl]-6,7,8,9-tetrahydropyrido[1,2-a]indole dihydrochloride,
6-Oxo-10-[2-(1-methyl-4-piperidyl)aminoethyl]-6,7,8,9-tetrahydropyrido[1,2-a]indole dihydrochloride,
6-Oxo-10-[2-(1-thienylmethyl)aminoethyl]-6,7,8,9-tetrahydropyrido[1,2-a]indole,
10-(2-Aminoethyl)-6,7,8,9-tetrahydropyrido[1,2-a]indole,
10-[2-Benzylaminoethyl]-6,7,8,9-tetrahydropyrido[1,2-a]indole,
2-Methyl-10-(2-benzylaminoethyl)-6,7,8,9-tetrahydropyrido[1,2-a]indole,
10-(2-Aminoethyl)-5a,6,7,8,9,10-hexahydropyrido[1,2-a]indole dihydrochloride, 10-(2-Benzylaminoethyl)-5a,6,7,8,9,10-hexahydropyrido[1,2-a]indole dihydrochloride,
10-[2-(3-Aminobenzyl)aminoethyl]-6,7,8,9-tetrahydropyrido[1,2-a]indole dihydrochloride,
6-Oxo-10-[2-(3,4-Methylenedioxybenzyl)aminoethyl]-6,7,8,9-tetrahydropyrido[1,2-a]indole,
10-[2-(3,4-Methylenedioxybenzyl)aminoethyl]-6,7,8,9-tetrahydropyrido[1,2-a]indole,
6-Oxo-10-[2-(2-nitrophenyl)aminoethyl]-6,7,8,9-tetrahydropyrido[1,2-a]indole,
6-Oxo-10-[2-(4-aminophenyl)aminoethyl]-6,7,8,9-tetrahydropyrido[1,2-a]indole,
6-Oxo-10-[2-(2-aminophenyl)aminoethyl]-6,7,8,9-tetrahydropyrido[1,2-a]indole,
10-[2-(4-Aminophenyl)aminoethyl]-6,7,8 9-tetrahydropyrido[1,2-a]indole dihydrochloride,
10-[2-(2-Aminophenyl)aminoethyl]-6,7,8,9-tetrahydropyrido[1,2-a]indole dihydrochloride,
10-[2-(3-Pivalylaminobenzyl)aminoethyl]-6,7,8,9-tetrahydropyrido[1,2-a]indole dihydrochloride,
10-[2-(3-Piperidinobenzyl)aminoethyl]-6,7,8,9-tetrahydropyrido[1,2-a]indole,
10-[2-(3-Diisopropylaminobenzyl)aminoethyl]-6,7,8 9-tetrahydropyrido[1,2-a]indole,
10-[2-(3-Pyrrolidinobenzy)aminoethyl]-6,7,8,9-tetrahydropyrido[1,2-a]indole,
10-[2-(3-Diethylaminobenzyl)aminoethyl]-6,7,8,9-tetrahydropyrido[1,2-a]indole dihydrochloride, or
10-[2-(4-Diethylaminobenzyl)aminoethyl]-6,7,8,9-tetrahydropyrido[1,2-a]indole or a pharmaceutically acceptable salt thereof.

16. A compound of the formula (Vc):

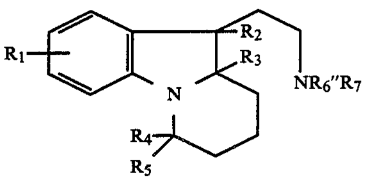

(Vc)

wherein $R_6''$ is phenyl $C_{1-7}$ alkanoyl optionally substituted as defined for the phenyl moiety in $R_6$ of claim 1 and the remaining variables are as defined in claim 1.

17. 6-Oxo-10-[2-(3-aminobenzoyl)aminoethyl]-6,7,8,9-tetrahydropyrido[1,2-a]indole,
6-Oxo-10-[2-(3-piperidinobenzoyl)aminoethyl]-6,7,8,9-tetrahydropyrido[1,2-a]indole,
6-Oxo-10-[2-(3-diisopropylaminobenzoyl)aminoethyl]-6,7,8,9-tetrahydropyrido[1,2-a]indole,
6-Oxo-10-[2-(3-pyrrolidinobenzoyl)aminoethyl]-6,7,8,9-tetrahydropyrido[1,2-a]indole,
6-Oxo-[2-benzoylaminoethyl]-6,7,8,9-tetrahydropyrido[1,2-a]indole,
6-Oxo-10-[2-(3-dimethylaminobenzoyl)aminoethyl]-6,7,8,9-tetrahydropyrido[1,2-a]indole, or
2-Methyl-6-oxo-10-(2-benzoylaminoethyl)-6,7,8,9-tetrahydropyrido[1,2-a]indole.

18. A compound of formula (Vd):

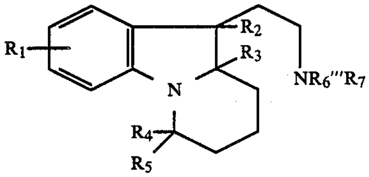

wherein $R_6'''$ is phenyl $C_{1-4}$ alkyl or phenyl $C_{1-4}$ alkanoyl mono-substituted by a protected amino group selected from the group consisting of $C_{1-6}$ alkoxycarbonyl, aryloxycarbonyl, $C_{1-6}$ alkanoyl and phenyl-$C_{1-7}$ alkanoyl or mono-substituted in the meta or para position by a nitro group, and the remaining variables are as defined in claim 1.

19. 6-Oxo-10-[2-(3-nitrobenzoyl)aminoethyl]-6,7,8,9-tetrahydropyrido[1,2-a]indole,
6-Oxo-10-[2-(3-pivaloylaminobenzoyl)aminoethyl]-6,7,8,9-tetrahydropyrido[1,2-a]indole,
6-Oxo-10-[2-(3-acetamidobenzoyl)aminoethyl]-6,7,8,9-tetrahydropyrido[1,2-a]indole,
6-Oxo-10-[2-(3-formamidobenzoyl)aminoethyl]-6,7,8,9-tetrahydropyrido[1,2-a]indole,
6-Oxo-10-[2-(4-nitrobenzyl)aminoethyl]-6,7,8,9-tetrahydropyrido[1,2-a]indole, or
6-Oxo-10-[2-(4-acetylaminobenzyl)aminoethyl]-6,7,8,9-tetrahydropyrido[1,2-a]indole.

20. A method of treatment of cerebrovascular disorders or disorders associated with cerebral senility in mammals including humans, which comprises administering to the sufferer a therapeutically effective amount of a compound of formula (I) as defined in claim 1 or a pharmaceutically acceptable salt thereof.

21. A composition for the treatment of cerebrovascular disorders or disorders associated with cerebral senility in mammals including humans, comprising a therapeutically effective amount of a compound of formula (I) or a pharmaceutically acceptable salt thereof:

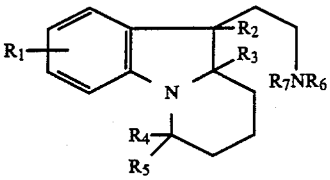

(I)

wherein:

$R_1$ is hydrogen, $C_{1-6}$ alkyl, $C_{1-6}$ alkoxy or halogen;

$R_2$ and $R_3$ are both hydrogen or together represent a bond;

$R_4$ is hydrogen and $R_5$ is hydrogen or $R_4$ and $R_5$ together represent an oxo group;

$R_6$ is hydrogen; $C_{1-6}$ alkyl; $C_{3-7}$ cycloalkyl; $C_{3-7}$ cycloalkyl-$C_{1-4}$ alkyl; phenyl or phenyl $C_{1-7}$ alkyl in which the phenyl moiety is optionally substituted by one or two of halogen, ortho-nitro, meta- or para-methoxy, methyl or $NR_8R_9$ wherein $R_8$ and $R_9$ are independently hydrogen or $C_{1-6}$ alkyl or $R_8$ and $R_9$ together form polymethylene of 2 to 6 carbon atoms, or the phenyl moiety is 3,4-disubstituted by methylenedioxy or ethylenedioxy; heteroaryl-$C_{1-4}$ alkyl, wherein said heteroaryl moiety is pyridyl, thienyl, furyl or optionally N-methyl substituted pyrryl; or aliphatic heterocyclyl or aliphatic heterocyclyl-$C_{1-4}$ alkyl, wherein said aliphatic heterocyclyl moiety is optionally N-methyl substituted piperidyl or optionally N-methyl substituted pyrrolidinyl; and $R_7$ is hydrogen or $C_{1-4}$ alkyl;

and a pharmaceutically acceptable carrier.

22. A composition for the treatment of cerebrovascular disorders or disorders associated with cerebral senility in mammals including humans, comprising a therapeutically effective amount of a compound of formula (II) or a pharmaceutically acceptable salt thereof:

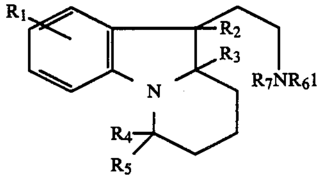

(II)

wherein $R_1$, $R_2$, $R_3$, $R_4$, $R_5$, and $R_7$ are as defined in claim 1 and $R_6$ is hydrogen, $C_{1-4}$ alkyl, $C_{5-7}$ cycloalkyl, or phenyl $C_{1-7}$ alkyl optionally monosubstituted by fluoro, chloro, bromo, $NR_8R_9$ and where $R_8$ and $R_9$ are as defined in claim 21, methoxy or nitro, and a pharmaceutically acceptable carrier.

* * * * *